(12) United States Patent
Reed et al.

(10) Patent No.: US 11,341,794 B2
(45) Date of Patent: May 24, 2022

(54) UNATTENDED TOUCHLESS HEALTH-CHECK SCREENING SYSTEMS INCORPORATING BIOMETRICS AND THERMOGRAPHIC TECHNOLOGIES

(71) Applicant: ZKTeco USA, Alpharetta, GA (US)

(72) Inventors: Lawrence Reed, Paterson, NJ (US); Manish Dalal, Clifton, NJ (US)

(73) Assignee: ZKTeco USA, Alpharetta, GA (US)

( * ) Notice: Subject to any disclaimer, the term of this patent is extended or adjusted under 35 U.S.C. 154(b) by 0 days.

(21) Appl. No.: 17/216,320

(22) Filed: Mar. 29, 2021

(65) Prior Publication Data

US 2021/0304537 A1   Sep. 30, 2021

Related U.S. Application Data

(60) Provisional application No. 63/009,699, filed on Apr. 14, 2020, provisional application No. 63/001,287, filed on Mar. 28, 2020.

(51) Int. Cl.
*G07C 9/00* (2020.01)
*G16H 10/20* (2018.01)
(Continued)

(52) U.S. Cl.
CPC ........ *G07C 9/00563* (2013.01); *G01J 5/0025* (2013.01); *G06K 9/6201* (2013.01);
(Continued)

(58) Field of Classification Search
CPC .. G07C 9/00563; G16H 10/20; G06V 40/171; G06V 40/172; G06V 40/15;
(Continued)

(56) References Cited

U.S. PATENT DOCUMENTS

| 7,455,224 B2 | 11/2008 | Kochevar et al. |
| 9,317,662 B2 | 4/2016 | Bangera et al. |

(Continued)

FOREIGN PATENT DOCUMENTS

| JP | 5446227 | 3/2014 |
| JP | 2019124012 | 7/2019 |
| WO | 2017057274 | 6/2017 |
| WO | 2017173639 | 12/2017 |
| WO | 2017173640 | 12/2017 |

*Primary Examiner* — Mohamed Barakat
(74) *Attorney, Agent, or Firm* — Doherty IP Law Group LLC

(57) ABSTRACT

An automated screening system includes an access control reader with one or more computer devices for screening a pre-registered individual seeking admittance into a controlled area. The system has a facial recognition database that stores a facial record for the individual. A camera system captures a facial image of the individual and the one or more computer devices determine whether it matches the facial record that is stored in the facial recognition database. A skin temperature sensor is used for obtaining a skin temperature reading for the individual. The one or more computer devices are configured to generate an electronic signal to admit the individual into the controlled area if the captured facial image matches the facial record that is stored in the facial recognition database and if the skin temperature reading for the individual is within an acceptable pre-established skin temperature range.

18 Claims, 35 Drawing Sheets

(51) Int. Cl.
  *G06K 9/62* (2022.01)
  *G08B 5/36* (2006.01)
  *G01J 5/00* (2022.01)
  *G06V 40/16* (2022.01)
  *G06K 19/06* (2006.01)
  *G06V 40/10* (2022.01)

(52) U.S. Cl.
  CPC .......... *G06V 40/171* (2022.01); *G06V 40/172* (2022.01); *G08B 5/36* (2013.01); *G16H 10/20* (2018.01); *G06K 19/06037* (2013.01); *G06V 40/15* (2022.01)

(58) Field of Classification Search
  CPC ................ G01J 5/0025; G06K 9/6201; G06K 19/06037; G08B 5/36
  See application file for complete search history.

(56) References Cited

U.S. PATENT DOCUMENTS

| | | | |
|---|---|---|---|
| 2006/0206724 A1* | 9/2006 | Schaufele | G07C 9/257 726/16 |
| 2008/0247609 A1* | 10/2008 | Feris | G06V 40/103 340/506 |
| 2013/0292467 A1* | 11/2013 | Avs | G07C 9/22 235/382 |
| 2015/0169169 A1* | 6/2015 | Andersson | G06F 3/0488 715/765 |
| 2019/0147676 A1* | 5/2019 | Madzhunkov | G06T 7/521 340/5.2 |
| 2019/0272413 A1* | 9/2019 | Eder | G06V 40/172 |
| 2019/0357857 A1* | 11/2019 | Tanaka | A61B 5/015 |
| 2020/0098209 A1* | 3/2020 | Zilka | G07C 9/00563 |
| 2020/0372743 A1* | 11/2020 | Miller | G06Q 20/40145 |

* cited by examiner

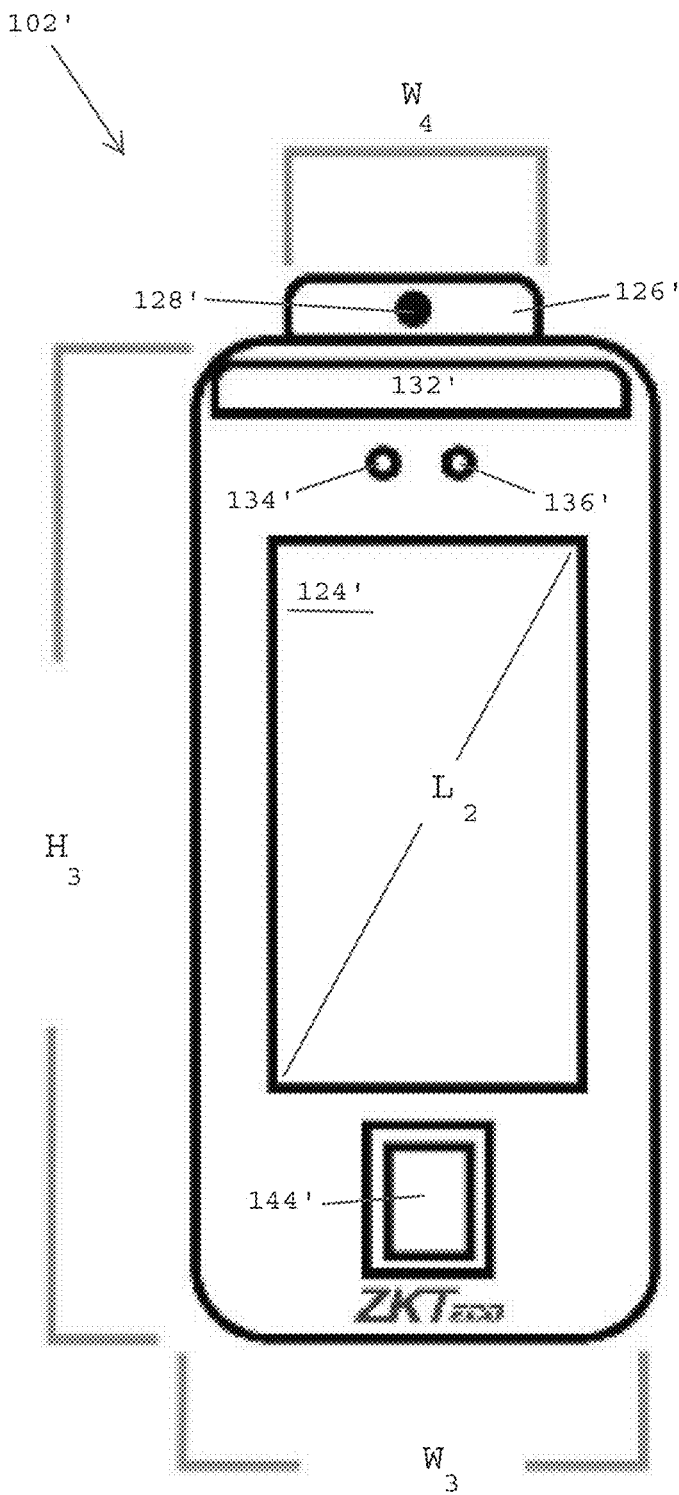
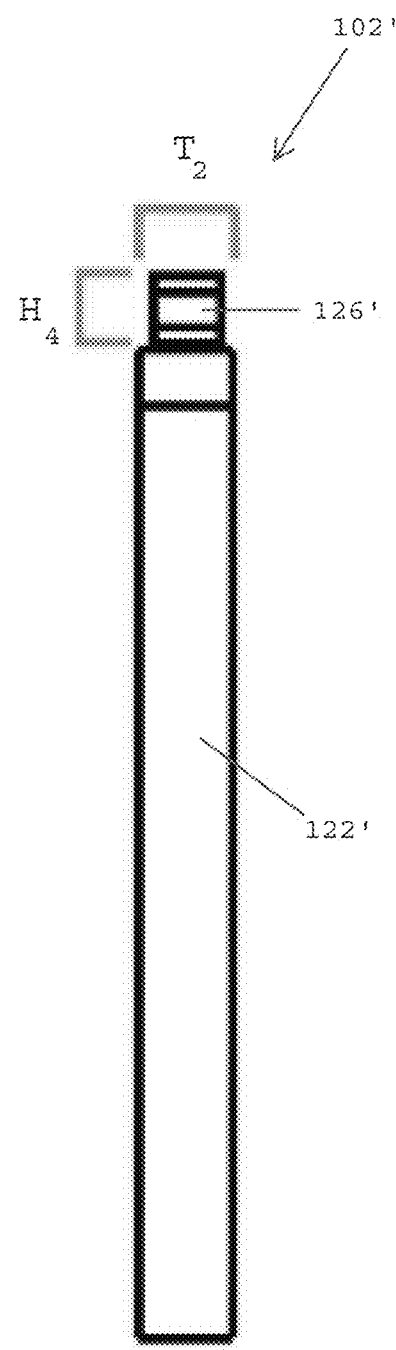
FIG. 5A
FIG. 5B

UNATTENDED TOUCHLESS HEALTH-CHECK SCREENING SYSTEMS INCORPORATING BIOMETRICS AND THERMOGRAPHIC TECHNOLOGIES

CROSS-REFERENCE TO RELATED APPLICATIONS

The present patent application claims benefit of U.S. Provisional Application No. 63/009,699, filed on Apr. 14, 2020, and U.S. Provisional Application No. 63/001,287, filed on Mar. 28, 2020, the disclosures of which are hereby incorporated by reference herein.

BACKGROUND OF THE INVENTION

Field of the Invention

The present patent application is generally related to the security industry and is more specifically related to system for screening visitors and controlling access to secure areas.

Description of the Related Art

The have been various developments related to monitoring employees and visitors for controlling access to enclosed spaces.

For example, JP2010128976 discloses an access control system for preventing a pathogen from entering a building and rooms when an infectious disease breaks out. The access control system includes an IC tag that is integrated into an employee identification to store and transmit a tag ID unique to the IC tag. A control server is installed in an internal area to transmit a message whether to permit passing of a gate to each antenna in response to an external message. Each antenna stores a unique antenna ID, and when the IC tag approaches, receives the tag ID, transmits it as well as the antenna ID to the control server, and opens each gate in response to the message from the control server. An infrared camera measures the body temperature of a person and transmits the body temperature data to the control server. An image recognition camera acquires face image data of the person to determine whether a mask is worn and transmits the determination result to the control server. A washstand W is used for the person to wash hands and transmits a message of hand washing to the control server.

JP2019124012 discloses an automatic door that is configured to prevent a person that is in bad health from entering a room. The automatic door has a health condition presumption section that presumes a health condition of a passenger based upon a combination of one or more variables including face color, gait, body surface temperature, heart rate, weight, and the odor of the passenger. The automatic door will open if the passenger satisfies the predetermined conditions to enter a room.

WO2017057274 discloses an elevator group management system. The system includes a security gate that is disposed at an entrance in a specific region of a building, which controls entry of a user of the building into the specific region. The security gate has a body temperature sensor that measures the body temperature of a user who is passing through the security gate. The system includes a security server that controls the opening and closing of a gate. When the body temperature measured by the body temperature sensor does not satisfy a predetermined body temperature condition, the security server controls the gate so that the entry of the user into the specific region is restricted.

U.S. Pat. No. 7,455,224 to Kochevar et al., the disclosure of which is hereby incorporated by reference herein, discloses a system for ensuring access management of a given site by providing integrated and comprehensive assessment of persons, livestock or objects that are given access to the site. The system includes a database of information about the site and potential accessors, a communication and scanning device to collect, retrieve and facilitate communication between the site as well as an administrator console. The system is flexible enough to maintain current information about the persons, livestock or objects requesting access to the site and communicating those results to the device user in real time. The system is further enabled through the Internet and the World Wide Web.

U.S. Pat. No. 9,317,662 to Bangera et al., the disclosure of which is hereby incorporated by reference herein, teaches methods, devices, and computer systems that are configured for automated data collection from a subject. In certain embodiments, one or more characteristics of a subject are sensed, and the subject is given a queue status indicator based on a comparison of the subject's one or more sensed characteristics with corresponding sensed characteristics from other subjects. In one embodiment, the subject is a healthcare worker, and the system, methods, and devices are utilized to evaluate the overall health of the worker as part of the check-in process for work.

There have also been advances in providing automated systems that monitor adherence to established protocols. For example, U.S. Pat. No. 10,361,000 to Johnson et al., the disclosure of which is hereby incorporated by reference herein, teaches a system for protocol adherence. The system provides an integrated and automated workflow, sensor, and reasoning system that automatically detects breaches in protocols, appropriately alarms and records these breaches, facilitates staff adoption of protocol adherence, and ultimately enables the study of protocols for care comparative effectiveness. The system provides real-time alerts to medical personnel in the actual processes of care, thereby reducing the number of negative patient events and ultimately improving staff behavior with respect to protocol adherence.

US 2016/0093127 to Evans, the disclosure of which is hereby incorporated by reference herein, discloses an entry point validation system. The system is implemented at entry points to controlled access areas, such as ticketed events, venues, buildings, rooms, elevators, and the like. One embodiment includes receiving a beacon identifier on a mobile device from a beacon device associated with an entry point. This embodiment includes transmitting, via a network from the mobile device, the beacon identifier and at least one identifier to a backend system with an entry request to electronically cause a credential to be provided to a computing device associated with an entry point.

U.S. Pat. No. 7,856,558 to Martin et al., the disclosures of which is hereby incorporated by reference herein, teaches a biometric verification and duress detection system. The system includes a first and second identification device to verify the identity of the user and to determine if the user is under duress. When a user approaches an entrance to a building, a first identifier is detected by the first identification device, and the first identifier is compared to a pre-stored identifier. If there is a match, the user inputs at least one biometric input into the second identification device. The biometric input is compares with pre-stored information in two different databases, a biometric template database and a duress indicator database. If there is a match with the duress indicator database, a silent alarm signal is transmitted to a central monitoring station and the security system is disarmed. If there is a match with the biometric template database, the security system is controlled in the intended manner.

US 2016/0248782 to Troesch, the disclosure of which is hereby incorporated by reference herein, teaches a system for controlling access by using portable electronic devices. The access control system is configured to detect the presence of a portable electronic device carried by a user in a first area. The access control system sends an access code to the device. In a second area, the user presents the portable electronic device to an access terminal, which reads the access code from the device. If the access code read from the device matches the access code that was sent to the device by the system, then the access control system grants access to the user.

U.S. Pat. No. 9,552,684 to Bacco et al., the disclosure of which is hereby incorporated by reference herein, teaches a security system that integrates physical and logical security controls for the protection of secured resources. The resources may include physical locations and/or computing resources such as databases containing personal information. In some embodiments, information is stored in separate, codependent databases such that by isolating the components of the databases from each other, a successful attack on one component is not sufficient to enable the access of content of the other components. In some embodiments, biometric information is automatically obtained as users approach an access location and is ready for expedited verification of identity upon request by the user.

Despite the above advances, there is a continuing need for improved access control systems, including automated touchless health-check screening systems that incorporate biometric and thermographic technology.

SUMMARY OF THE INVENTION

The process of entering a secure facility can consume time and overlook health guidelines putting people at risk. In one embodiment, an access control system is adapted to verify an employee's or visitor's identity and scheduled appointment, verify that their health check questionnaire is completed and approved, ensure acceptable skin temperature, confirm mask usage, and detect concealed metal objects, thereby making the check-in process 100% automated, touchless, and safe.

In one embodiment, prior to visitors arriving for an appointment, a host will send an invitation to the visitor's phone, which contains a unique QR code. When the visitor arrives, the QR code is presented to a visitor management kiosk. The QR code contains information about the visitor and the visitor's scheduled appointment. The visitor management kiosk scans and validates the visitor's identity and scheduled appointment. Next, the visitor management kiosk scans the visitor's skin temperature to ensure it is within the kiosk operator's user-defined acceptable range. In one embodiment, the operator may define and establish the kiosk's temperature alarm setting. The visitor management kiosk will also check to ensure that the visitor is wearing a protective face mask. After the kiosk confirms the visitor's identity and scheduled appointment, records an acceptable skin temperature, and confirms that they are wearing a protective mask, the kiosk will print an admittance ticket for the visitor. Simultaneously, the kiosk generates an electronic message that notifies the host that the visitor has arrived and is permitted to enter the facility. In one embodiment, the operator of the system may either activate or deactivate, separately or collectively, all the above-described parameters.

In one embodiment, a visitor then approaches a physical barrier (e.g., a turnstile, gate, door, elevator, etc.) where an access control reader verifies the visitor's identity with image or biometric recognition technology (e.g., fingerprint, finger-vein, face, palm vein, palm print, iris, retina, voice, etc.), thereby eliminating the need for carrying an ID card. The access control reader may also conduct a skin temperature check to confirm that the visitor's temperature is within an acceptable range, while additionally scanning for face mask compliance. An operator-defined health-check questionnaire can also be displayed on the access control reader which requires the visitor to satisfactorily answer. Visitors may respond to the access control reader's on-screen questionnaire by using either the access control reader's touch-screen display, or by instead using touchless external motion-sensors connected to the access control reader. Once identity and acceptable skin temperature are confirmed, along with all the above-described parameters, the physical barrier (e.g., turnstile, gate, door, elevator, etc.) will release allowing the visitor to proceed to a walkthrough metal detector. In one embodiment, the operator of the system may either activate or deactivate, separately or collectively, all the above-described parameters. In one embodiment, the barrier may also incorporate metal detection technology.

In one embodiment, a walkthrough metal detector preferably includes two vertical panels which have upper ends that are held together at the top of a control module. Each of the two panels contain LED lights. At the front side of the walkthrough metal detector, the visitor will position their forehead or wrist within six inches of a skin temperature thermal scanner. Thermal scanning takes less than two seconds. The control module displays each visitor's skin temperature. If no elevated temperature is detected, the visitor can proceed through the walkthrough metal detector. If a metal object is detected, the nearest LED light to the object will illuminate and an alarm will sound. If no metal object is detected, visitors are then allowed to enter the facility with their host.

In one embodiment, a combination of an access control reader and a physical barrier (e.g., a turnstile, gate, door, elevator, etc.) may be used to verify a visitor's identity and ensure an acceptable skin temperature prior to allowable access to a controlled area. The process is quick and simple. First, users approach the physical barrier. The access control reader will verify the visitor's identity with image or biometric recognition technology (e.g., fingerprint, finger-vein, face, palm-vein, palm print, iris, retina, voice, etc.), thereby eliminating the need for carrying an ID card. The device will also conduct a skin temperature check to confirm that it is within an acceptable range. Once identity and acceptable skin temperature are confirmed, the physical barrier will release allowing the user to enter the facility.

In one embodiment, an access control system may include a walkthrough metal detector that can detect concealed metal objects using multiple (e.g., 3, 6, 18, 33) detection zones. The walkthrough metal detector also preferably includes a skin temperature scanner for detecting a visitor's skin temperature. The process is simple. First, user's position their forehead or wrist within six inches of the skin temperature scanner. Thermal scanning takes less than two seconds. If no elevated temperature is detected, the user can proceed through the walkthrough metal detector. If a metal object is detected, the nearest LED light to the object will illuminate and an alarm will sound. Upon positive detection, an attendant will then pull the user aside and scan them with a handheld metal detector to reveal and remove the concealed object. If no metal object is detected, users are permitted to enter the facility.

In one embodiment, an access control system preferably includes a visitor management kiosk that can verify a visitor's identity and scheduled appointment, ensure that the visitor has an acceptable skin temperature, and confirm that the visitor is wearing a protective mask, all while recording the entire process for auditing and reporting purposes. In one embodiment, prior to a visitor arriving for their appointment, their host will send an invitation to the visitor's phone which contains a unique QR code. Creating the invitation is quick and easy. When the visitor arrives, they display their QR code to the visitor management kiosk. The kiosk then scans the visitor's skin temperature to ensure that it is within an acceptable range. If selected as a requirement, the visitor management kiosk will also check to ensure that the visitor is wearing a protective face mask. After the kiosk confirms the visitor's identity, appointment, acceptable skin temperate and that they are wearing a mask, the kiosk will print an admittance ticket for the visitor. Simultaneously, the kiosk notifies the host that the visitor has arrived and is permitted to enter the facility.

In one embodiment, when the walkthrough metal detector detects a metal object, it produces an audible and visual alarm for the metal object on the side of the walkthrough metal detector corresponding to where the metal object is on the person, which provides a visual and audible indicator to the security guard regarding precisely where the metal object is located on the person so that the guard can quickly wand the person with a handheld metal detector, locate/remote the metal object, and allow the person and everyone waiting behind the visitor to proceed onward.

In one embodiment, the sensitivity of the walkthrough metal detector may be modified. If the walkthrough metal detector is deployed in a correctional facility, the sensitivity may be turned to a highest level. If the walkthrough metal detector is deployed in a school or at a concert, it might be turned to mid-range sensitivity.

In one embodiment, an automated system for screening individuals preferably includes an access control reader including one or more computer devices configured for screening a pre-registered individual seeking admittance into a controlled area.

In one embodiment, the one or more computer devices contain a facial recognition database that stores a facial record for the pre-registered individual.

In one embodiment, a camera system is preferably configured to capture a facial image of the pre-registered individual, whereby the one or more computer devices evaluate the captured facial image for determining whether the captured facial image matches the facial record of the pre-registered individual that is stored in the facial recognition database.

In one embodiment, the system desirably includes a skin temperature sensor for obtaining a skin temperature reading for the pre-registered individual.

In one embodiment, the one or more computer devices are configured to generate an electronic signal to admit the pre-registered individual into the controlled area if 1) the captured facial image matches the facial record of the pre-registered individual that is stored in the facial recognition database, and 2) the skin temperature reading for the pre-registered individual is within an acceptable skin temperature range established for the automated system. If the pre-registered individual fails either test, then access is denied, and an alert message may be transmitted to security.

In one embodiment, the system may include an authenticating information generator that generates authenticating information that is used for confirming the identity of the pre-registered individual seeking admission to the controlled area.

In one embodiment, the authenticating information generator may be a QR code generator that is configured for transmitting a QR code to the pre-registered individual.

In one embodiment, the access control reader may include a QR code reader that is configured to scan the QR code that is transmitted to the pre-registered individual for confirming the identity of the individual.

In one embodiment, the QR code generator is configured for transmitting the QR code to the pre-registered individual in an electronic format that is adapted for being displayed on an electronic device, such as a mobile phone. In one embodiment, the QR code may be printed onto a paper sheet that is scanned using the access control reader.

In one embodiment, the one or more computer devices may operate software that is configured for analyzing the captured facial image for confirming whether the pre-registered individual is wearing a protective mask.

In one embodiment, the one or more computer devices authorize admission into the controlled area upon confirming that the pre-registered individual is wearing the protective mask.

In one embodiment, the one or more computer devices deny admission into the controlled area upon confirming that the pre-registered individual is not wearing the protective mask.

In one embodiment, the camera system may include a first camera configured to capture a first facial image of the pre-registered individual within the visible light spectrum.

In one embodiment, the camera system may include a second camera configured to capture a second facial image of the pre-registered individual within the infrared light spectrum.

In one embodiment, the captured first and second facial images may be processed by the one or more computer devices for determining that the captured first and second facial images match the facial record of the pre-registered individual that is stored in the facial recognition database.

In one embodiment, a visitor management kiosk may contain the access control reader.

In one embodiment, a system may include a printer that is configured to print an admittance ticket or badge for the pre-registered individual after the pre-registered individual has been authorized for admission into the controlled area.

In one embodiment, the visitor management kiosk may include a stand and a ticket issuing slot may be formed in the stand for dispensing the admittance ticket or badge.

In one embodiment, the one or more computers may include a software protocol for transmitting an alert message to a host for notifying the host that the pre-registered individual has been authorized admission into the controlled area.

In one embodiment, the one or more computer devices may contain software for a health-check screening questionnaire that is used for evaluating the health status of the pre-registered individual.

In one embodiment, the pre-registered individual is authorized admittance into the controlled area if completion of the health-check screening questionnaire indicates that the pre-registered individual is healthy as defined by a predetermined standard.

In one embodiment, the pre-registered individual is denied admittance into the controlled area if competition of the health-check screening questionnaire indicates that the pre-registered individual is unhealthy as defined by the predetermined standard.

In one embodiment, the one or more computer devices may include a biometric database that stores a biometric record for the pre-registered individual.

In one embodiment, the system may include a biometric scanner for capturing biometric information about the pre-registered individual seeking admittance into the controlled area.

In one embodiment, the one or more computer devices generate a signal to admit the pre-registered individual into the controlled area if the captured biometric information matches the biometric record of the pre-registered individual that is stored in the biometric database.

In one embodiment, different types of biometric information may be used including but not limited to fingerprints, finger-vein patterns, facial patterns, palm vein patterns, palm prints, iris images, retina images, and voice recordings.

In one embodiment, the skin temperature sensor may include thermal sensors, sensors incorporating thermographic imaging technology, and/or sensors incorporating thermopile technology.

In one embodiment, an access control reader may include a visual display having a first region for displaying the captured image of the pre-registered individual.

In one embodiment, the visual display may include a second region for displaying a thermal image of the pre-registered individual that has been captured by a skin temperature sensor.

In one embodiment, the system may include a physical barrier that is in communication with the access control reader.

In one embodiment, the physical barrier is moveable between a first position in which the pre-registered individual is prevented from proceeding toward the controlled area and a second position in which the pre-registered individual is free to pass through the physical barrier for proceeding toward the controlled area.

In one embodiment, the physical barrier may be a turnstile, gates, doors, and/or elevators.

In one embodiment, the system may include a metal detector having first and second vertical panels having upper ends that are joined together by a control module that extends between the upper ends of the two vertical panels.

In one embodiment, the metal detector is adapted to detect metal passing between the first and second vertical panels.

In one embodiment, the first vertical panel has a front side including a first LED light array that extends along the front side of the first vertical panel.

In one embodiment, the second vertical panel has a front side including a second LED light array that extends along the front side of the second vertical panel.

In one embodiment, the metal detector may include a skin temperature sensor secured to the second vertical panel for obtaining a skin temperature reading for the pre-registered individual.

In one embodiment, the metal detector preferably illuminates at least one LED light of the first and second LED light arrays if a metal object is detected between the first and second vertical panels.

In one embodiment, upon detecting a metal object passing between the first and second vertical panels, the metal detector is configured to illuminate an LED light that is nearest to the metal object. For example, if the metal object is located on the left side of an individual passing through the metal detector, one or more of the LEDs on the first vertical panel will illuminate and none of the LEDs on the second vertical panel will illuminate. Similarly, if the metal object is located on the right side of an individual passing through the metal detector, one or more of the LEDs on the second vertical panel will illuminate and none of the LEDs on the first vertical panel will illuminate. Thus, tending security may rapidly determine where the metal object is located on the individual passing through the metal detector.

In one embodiment, a computer-implemented method of controlling access to a controlled area may include before screening an individual for admittance into a controlled area, storing a facial image for the individual in a facial image database of a computer device, storing biometric information for the individual in a biometric information database of the computer device, assigning authenticating information to the individual, and transmitting the authenticating information to an electronic device that is under the control of the individual.

In one embodiment, a computer-implemented method of controlling access to a controlled area may include while screening the individual for admittance into the controlled area, scanning the electronic device under the control of the individual to retrieve the authenticating information for confirming the identity of the individual, capturing a new facial image of the individual, capturing new biometric information for the individual, and obtaining a skin temperature reading for the individual In one embodiment, a computer-implemented method of controlling access to a controlled area may include generating a signal for authorizing admittance of the individual into the controlled area if 1) the authenticating information retrieved from the electronic device matches the transmitted authenticating information, 2) the captured new facial image matches the stored facial image, 3) the captured new biometric information matches the stored biometric information, and 4) the obtained skin temperature reading for the individual is within a predetermined acceptable temperature range.

In one embodiment, an access control, monitoring, and authentication system preferably includes a sensor adapted to detect an individual's skin temperature and the skin temperature information may be used to control the operation of one or more electronic devices.

In one embodiment, when authenticating an individual using an electronic device, the access control, monitoring, and authentication system may automatically record an individual's skin temperature.

In one embodiment, when authenticating an individual using an electronic device and/or when an unacceptable skin temperature is detected (e.g., a user-defined unacceptable skin temperature), the access control, monitoring and authentication system is preferably programmed to automatically generate and/or transmit electronic alerts or messages (e.g., text messages, e-mail messages, voice mail messages) to a central processing unit or monitoring station.

In one embodiment, an access control, monitoring, and authentication system preferably includes an image or biometric detection device that is adapted to detect user's credentials (e.g., fingerprint, finger-vein, face, palm-vein, palm print, iris, retina, voice, etc.) of a plurality of individuals (e.g., employees). In one embodiment, the monitoring system may also be used for detecting the presence of individuals at a physical location (e.g., as a punch clock for hourly wage employees)

In one embodiment, an access control, monitoring, and authentication system preferably detects the presence of an individual at a location and preferably records the date, the time, the employee's name and assigns an identification number to the transaction, which may be referred to as a time stamp.

In one embodiment, an access control, monitoring, and authentication system preferably includes software that aggregates the employee's time stamps and calculates the total number of work hours for the employee during a designated pay period. The system may calculate payroll information for an employee by multiplying the total number of hours worked by the employee by the hourly pay rate for the employee.

In one embodiment, an access control, monitoring, and authentication system preferably sends the payroll information to a payroll company and/or a payroll application, which desirably produces the employee's paycheck.

In one embodiment, an access control, monitoring, and authentication system is adapted to monitor and record an employee's work attendance record, and desirably includes a skin temperature sensor. In one embodiment, after the employee's skin temperature is recorded, the skin temperature information is added to the employee's time stamp.

In one embodiment, if upon "punching in" the employee's sensed skin temperature is above or below the employers user configurable temperature range (e.g., 97-100 degrees Fahrenheit may be programmed into the system as being an acceptable skin temperature) an alert message may be transmitted via text message, e-mail, and/or voice mail to alert company personnel (e.g., a human resources manager; an on-site manager) that an employee has an unacceptable skin temperature.

In one embodiment, an access control, monitoring, and authentication system may generate a message that the employee is not qualified to work at the site and must immediately exit the location (e.g., the building) to not risk infecting others with a contagious disease (e.g., a virus; the flu).

In one embodiment, if it is determined that one or more employees or students are sick, an organization's, company's or school's time stamp records may be searched to analyze which, if any, individuals have "punched in" while having an unacceptable skin temperature, which may generate a contact tracing protocol.

In one embodiment, an access control, monitoring, and authentication system preferably includes sensors that record biometric data from individuals seeking to gain access to a controlled environment (e.g., a building; a factory; a school). The system utilizes the biometric data to determine whether the individuals may be granted access to the controlled environment. In one embodiment, the system also preferably records the skin temperatures of individuals passing through the authentication station and creates a record of the skin temperature readings that are linked to the individuals. In one embodiment, if an unacceptable skin temperature is recorded, the system desirably generates one or more alert messages to provide a notification that an unacceptable skin temperature reading has been recorded.

In one embodiment, an access control, monitoring, and authentication system preferably controls physical access to a controlled environment, records skin temperature readings with employee time and attendance records, and records visitors having unacceptable skin temperatures.

Current visitor management systems typically include either a written logbook at a reception/security desk, or more recently electronic systems that send electronic invitations to the phones or electronic devices of visitors, such as identification numbers or QR codes. Upon arrival, the visitor normally shows his or her identifying information (e.g., driver's license, identification number, QR code, etc.) to a receptionist or security guard. The identifying information is recorded into an electronic audit log (kiosk/computer).

In one embodiment, an access control, monitoring, and authentication system preferably records a visitor's skin temperature when the visitor checks in. If the visitor's skin temperature falls outside an acceptable skin temperature range, an alert may be sent to a building security officer. In one embodiment, if it is determined that one or more individuals at a location become ill, the system preferably provides and/or conducts an audit log analysis to determine whether any visitors had an elevated skin temperature. In one embodiment, health officials and/or on-site personnel may be notified of the presumed "sick" visitor's identification.

In one embodiment, access control, monitoring and authentication system may be used to control access to a location or an electronic device (e.g., physical barriers; anything electronic such as an ignition switch for a car or appliance; accessing the ability to use a computer or communication device).

In one embodiment, an access control, monitoring, and authentication system may be used to record and maintain time and attendance records, and record and maintain a visitors' log.

In one embodiment, an access control, monitoring, and authentication system preferably records individuals' skin temperatures and generates alerts upon detecting unacceptable skin temperatures. The system may be used for event management, patient management, point of sales systems, withdrawing money from an ATM, and any application that requires an individual to provide identification before they can proceed further with their desired transaction.

In one embodiment, an access control, monitoring, and authentication system may be used by officials (e.g., local health officials) to identify individuals who may have unacceptable skin temperatures (e.g., high fever) to limit the spread of infectious diseases among the public.

In one embodiment, an access control, monitoring, and authentication system is preferably adapted to authenticate individuals by using one or more sensors to record and store an individual's biometric data and match the recorded information with matching data such as an individual's credentials (e.g., a PIN; an ID card #; biometric data; skin temperature).

In one embodiment, upon detecting a match, the access control, monitoring, and authentication system may:

1) Open an onboard electric relay, which supplies electricity to one or more electro-mechanical devices (e.g., a door; a gate; an elevator; a forklift; a vehicle; an HVAC system; and/or 2) Transmit an individual's ID # to an external controller, whereupon the controller preferably opens a relay to one or more electro-mechanical devices; and/or 3) Transmit the "transaction" information (e.g., device ID #, individual's ID #, individual's name; date; time; skin temperature; face mask on/off?) to an external software database (e.g., time and attendance programs; payroll systems; event management systems) or any other application that may require user authentication).

In one embodiment, the entire system may be contained within a stand-alone electronic device that does not require an external server. Thus, all the access and monitoring operations disclosed herein may be performed "onboard" the device, without requiring an external connection.

In one embodiment, a system for controlling access to a controlled area preferably restricts access to the controlled area via a physical barrier (e.g., a turnstile) based upon one or more factors including an individual's skin temperature, whether the individual is wearing a protective mask (i.e., compliance), and/or whether the individual presents proper biometric credentials.

In one embodiment, a system for controlling access to a controlled area may be configured to control any type of electrical device based upon one or more factors including an individual's skin temperature, whether the individual is wearing a protective mask (i.e., compliance), and/or whether the individual presents proper biometric credentials.

In one embodiment, a system for controlling access to a controlled area may include methodologies for matching an hourly-wage employee's skin temperature with their date/time stamp when punching in/out of work.

In one embodiment, a system for controlling access to a controlled area may combine visitor management, health check screening, people counting and occupancy control, access control, and/or metal detection into a single solution.

In one embodiment, a screening system may use QR codes to validate an individual's identity and/or that the individual has a scheduled appointment.

In one embodiment, a system for controlling access to a controlled area may use skin temperature readings to control any electrical motor (e.g., to provide physical access) or computer/network (e.g., logical access).

In one embodiment, a system for controlling access to a controlled area may use biometrics for both recording purposes and physical (e.g., doors/gates) and logical (e.g., computers) access control.

In one embodiment, a system for controlling access to a controlled area preferably can detect if a mask is being worn and/or recognize/authenticates the person wearing the mask.

In one embodiment, a system for controlling access to a controlled area preferably uses individual or any combination of PINs, card IDs, biometrics and/or body temp to authenticate a user for either physical (e.g., gate) or logical access.

In one embodiment, a system for controlling access to a controlled area preferably utilizes the presence of a mask to control physical (e.g., gate) and logical (e.g., computer) access. The system may also recognize/authenticate the person wearing the mask In one embodiment, a system for controlling access to a controlled area may record "door access events" and/or transmit electronic alerts to authorities (e.g., work supervisors, school administrators, and public health officials).

In one embodiment, a system for controlling access to a controlled area may combine skin temperature detection with walkthrough metal detectors and/or a combination of a metal detector and turnstiles.

In one embodiment, a system for controlling access to a controlled area may be capable of exporting data (e.g., time stamp; user ID; skin temperature) to third party business applications (i.e., Apps) including but not limited to Time and Attendance Apps, Visitor Management Apps, Point of Sales Apps, Event Management Apps, etc.

These and other preferred embodiments of the present patent application will be described in more detail below.

BRIEF DESCRIPTION OF THE DRAWINGS

FIG. 5A is a front elevation view of an access control reader of an access control system, in accordance with one embodiment of the present patent application.

FIG. 5B is a side view of the access control reader shown in FIG. 5A.

DETAILED DESCRIPTION OF PREFERRED EMBODIMENTS

Figure 1:
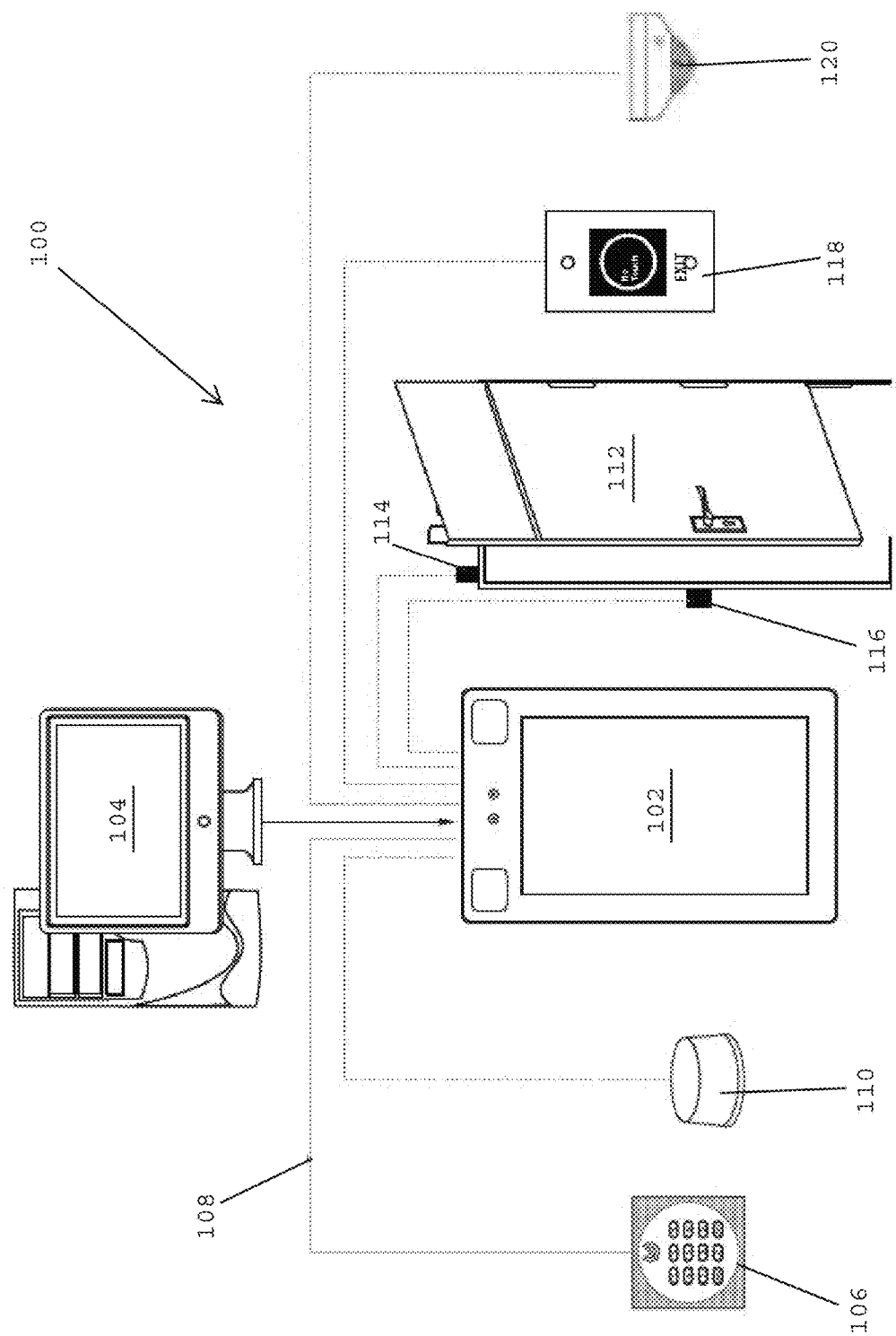
FIG. 1 is a schematic view of an access control system for monitoring and authenticating individuals prior to allowing the individuals access into controlled areas, in accordance with one embodiment of the present patent application.

Referring to FIG. 1, in one embodiment, an access control system 100 preferably includes an access control reader 102 that is preferably utilized to authenticate individuals and control access to controlled areas including but not limited to enclosed physical locations, research laboratories, manufacturing facilities, prisons, military installations, or factory floors. In one embodiment, the access control reader 102 is desirably in communication with and is controlled by a central controller 104 (e.g., a computer network) that may include one or more servers, one or more central processing units (CPUs), software, computer applications, video monitors, and computer monitors. The access control system may incorporate wired or wireless communication networks. In one embodiment, the system controller 104 may be used for establishing rules that are used to authenticate individuals and control and monitor access to controlled areas. In one embodiment, the access control reader 102 may operate standalone (e.g., without the system controller 104) and may be directly wired to both input and output peripheral electronic devices including but not limited to a keypad/card reader 106, an alarm 110, an electric door lock 116, a door/ajar sensor 114, an exit switch 118, or a surveillance camera 120.

As used herein, a central processing unit (CPU), also called a central processor, main processor or just a processor, is the electronic circuitry that executes instructions comprising a computer program. The CPU performs basic arithmetic, logic, controlling, and input/output operations specified by the instructions in the program.

In one embodiment, an operator of the access control system 100 may modify the number of rules that must be satisfied prior to authorizing an individual to have access to a controlled area. For example, gaining access to a nuclear site may require more rules to be satisfied, and gaining access to an office building may require fewer rules to be satisfied.

In one embodiment, the access control system 100 preferably includes a keypad/card reader 106 that is coupled with the access control reader 102 via a communication line 108. The keypad/card reader 106 may be configured to detect the presence of various types of hand-held cards that are used for gaining access to secured locations including but not limited to identification cards, building access cards, credit cards, and debit cards. In one embodiment, the communication line 108 between the card reader 106 and the access control reader 102 may incorporate various communication protocols including but not limited to the Wiegand communication protocol and/or the Open Supervised Device Protocol (OSDP). The keypad/card reader 106 represents only 1 of many different authentication technologies which can be used with the embodiment. Other authentication technologies may include Barcode, Mag Stripe, Bluetooth, Near-field communication (NFC), Ultrawide band (UWB), Ultra high frequency (UHF), Zigbee, Zwave, and artificial intelligence voice responders including Amazon Alexa, Apple Siri, and Google Assistant.

In one embodiment, the access control system 100 preferably includes an alarm 110 that may be activated if the system determines that an individual attempting to gain access to a controlled area fails one or more of the rules that have been established via the central control unit 104. For example, if the access control reader 102 detects that an individual attempting to gain access to a secure area has an unacceptable skin temperature (e.g., 103 degrees Fahrenheit), the access control reader 102 will send a signal to the alarm 110 to activate the alarm. In one embodiment, the alarm 110 may generate a visible alarm (e.g., flashing light) and/or an audible alarm (e.g., a loud, piercing siren sound).

In one embodiment, the access control system 100 may be coupled with a security component that is normally locked for preventing access to a controlled area, and that is unlocked to allow access to the controlled area. In one embodiment, the security component may be a door 112 having an electric lock 114 that is in communication with the access control reader 102. In one embodiment, if an individual engaging with the access control reader 102 satisfies the rules that have been established for being granted access to a controlled area, the access control reader 102 will transmit a signal to the electric lock 114 on the door 112 for moving the electric lock 114 to an open/unlocked position so that the door 112 may be opened.

In one embodiment, the access control system 100 preferably includes a door status sensor 116 that periodically senses and/or detects whether the door 112 is open or closed/locked. In one embodiment, if the door 112 remains open after a predetermined time (e.g., 30 seconds), the access control reader 102 will recognize that the door 102 is open and will send an alarm signal to the alarm 110.

In one embodiment, the access control system 100 preferably includes an exit controller 118 that is in communication with the access control reader 102. In one embodiment, the exit controller 118 may include a depressible button or a motion sensor for indicating when an individual wishes to exit an area that is enclosed by the door 112. In one embodiment, an individual may depress a button on the exit controller 118 for transmitting a signal to the access control reader 102, which, in turn, generates a signal for unlocking the electric lock 114 so that the door 112 may be opened.

In one embodiment, the access control system 100 may include a surveillance camera 120 that is in communication with the access control reader 102. In one embodiment, if the access control system 100 detects the door lock 114 has opened, the access control reader 102 can trigger the surveillance camera 120 to begin recording video (or take a snapshot) of whomever opened the door 112 and store the recorded video/snapshot in a database located on the central controller 104. The video/snapshot can subsequently be used for auditing and reporting purposes.

The system disclosed in FIG. 1 may be a standalone system that is not interconnected with a network. Thus, in one embodiment, the use of a computer and software may be optional. In one embodiment, the access control system 100 shown in FIG. 1 may be in communication with a network via wired communication, wireless communication and/or the internet so that one or more different locations may be controlled via a remote network controller that is not located at the same site as the access control reader 102.

Figure 2:
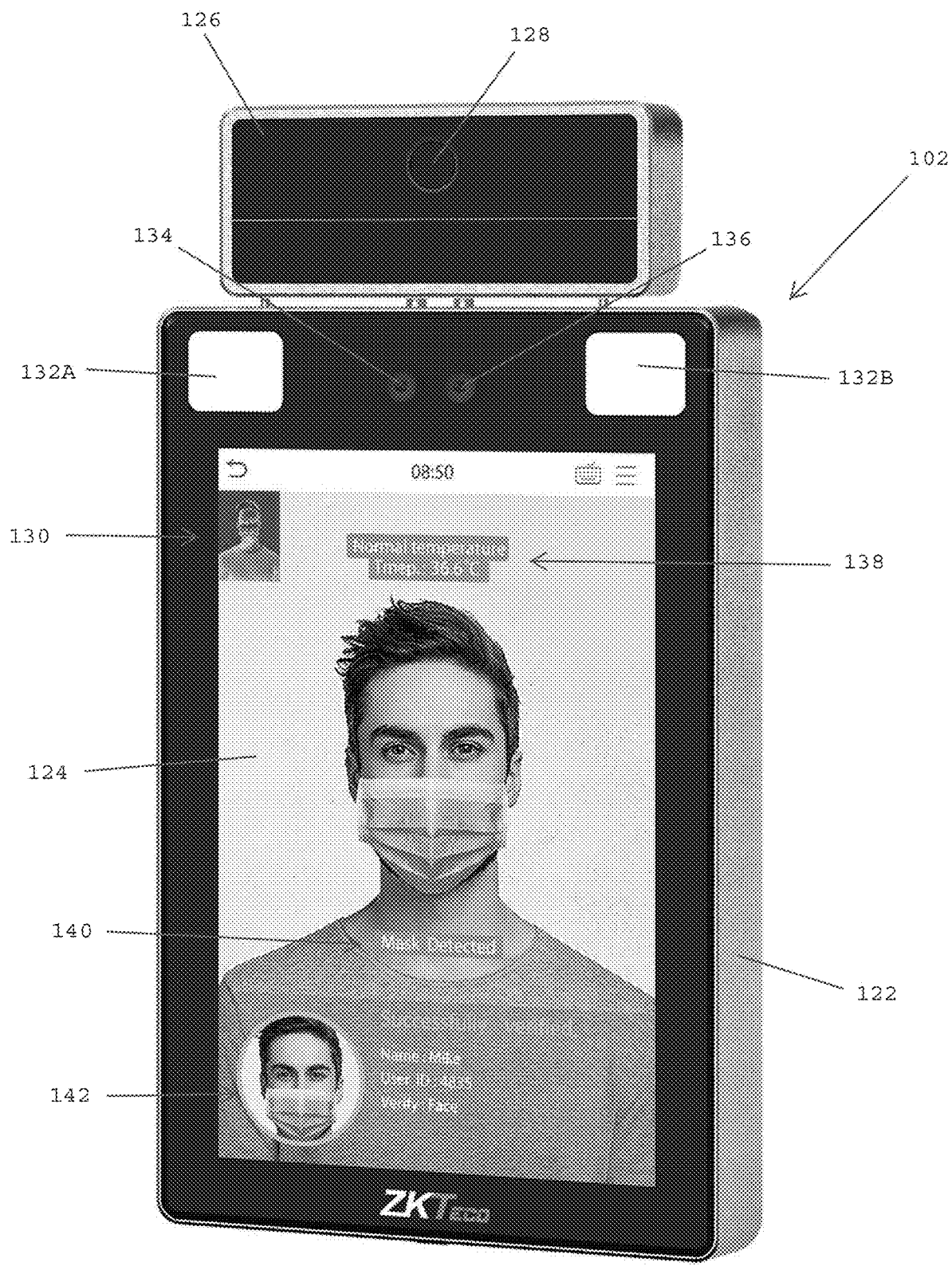
FIG. 2 is a perspective view of a front side of an access control reader of an access control system, in accordance with one embodiment of the present patent application.

Referring to FIG. 2, in one embodiment, the access control reader 102 preferably includes a housing 122 that contains a display screen 124 (e.g., video screen) that has touch-screen technology. In one embodiment, a thermal sensor may be used with the access control reader for obtaining skin temperature readings for employees and/or visitors.

In one embodiment, the access control reader 102 preferably includes a skin temperature sensor 126 including a thermal sensor 128 that may be utilized for detecting the skin temperature of an individual interacting with the access control reader 102. In one embodiment, the skin temperature sensor 126 may incorporate thermographic imaging technology or thermopile technology for obtaining skin temperature readings of individuals who stand in front of the skin temperature sensor 126. In one embodiment, the display screen 124 of the access control reader 102 includes a thermal image section 130 that shows a thermal image of the individual standing in front of the access control reader 102.

In one embodiment, the access control reader 102 preferably includes a first light emitting diode (LED) 132A and a second LED 132B that are utilized for generating light, which is illuminated onto an individual standing in front of the access control reader 102.

In one embodiment, the access control reader 102 preferably includes a dual camera lens design having a first camera 134 that detects light within the visible light spectrum and a second camera 136 that detects light within the infrared spectrum. In one embodiment, the infrared camera 136 is preferably utilized for obtaining infrared images of an individual, which are used by integrated face and palm recognition technology to confirm that the person standing in front of the access control reader 102 is the same person who has pre-registered his or her face and/or palm biometric template with the access control system 102.

In one embodiment, when an individual seeking to be authenticated stands in front of the access control reader 102, the skin temperature sensor 126 is utilized for obtaining a temperature reading for the individual. The skin temperature reading is displayed within a temperature reading section 138 of the visual display 124. In one embodiment, the individual's temperature and temperature status may be displayed within the temperature reading section 138. In one embodiment, the individual's skin temperature may be displayed in either Fahrenheit or Celsius). If an individual's temperature reading is within a user-defined acceptable temperature range, the temperature display section shows the temperature reading and the terminology "normal temperature" in a first color, such as green. If an individual's skin temperature reading is above a user-defined acceptable temperature range, the temperature reading section 138 displays both the individual's skin temperature reading and the terminology "high body temperature" within the temperature reading section 138 in a second color, such as red.

In one embodiment, the rules for the access control system 100 may be modified by the operator to select what is deemed to be an acceptable temperature (e.g., normal) and what is deemed to be an unacceptable temperature (e.g., high).

In one embodiment, the access control reader 102 may be utilized for determining whether an individual attempting to gain access to a controlled area is wearing a protective mask.

In FIG. 2, the individual being scanned by the dual camera lens design is shown within the display screen 124. In turn, the display screen 124 has a mask status section 140 that indicates the masking status of an individual. In one embodiment, if the access control reader 102 detects that an individual is wearing a protective mask, the mask status section 140 of the display screen will display the message "Mask Detected." In one embodiment, if the access control reader 102 detects that an individual is not wearing a protective mask, the mask status section 140 will display the message "Mask Not Detected."

In one embodiment, prior to attempting to gain access to a controlled area, an individual will pre-register with the access control system 100 (FIG. 1) by sending information to the system such as an electronic file of the individual's face picture 142. In FIG. 2, the individual's pre-registered face picture is shown in a pre-registered picture section 142 of the display screen 124.

In one embodiment, the display screen 124 of the access control reader 102 may also display other identifying information including the registered individual's name, identification number, and other pre-registration information.

In FIG. 2, the access control reader 102 has verified the face of the individual attempting to gain access by comparing the face shown on the main portion of the display screen 124 with the pre-registered picture of the individual that has been previously submitted by the user and that is shown in the pre-registered picture section 142.

In one embodiment, the access control reader 102 may provide audible and/or visible feedback in response to a determination of whether the individual has successfully satisfied the rules required for entry into a controlled area. In one embodiment, if an individual fails one or more of the rules required for entry into the controlled area, the access control reader 102 may generate an audible alarm and/or flashing lights (or display a red screen background) to indicate that the individual has failed one or more rules and may not be granted access into the controlled area.

In one embodiment, the alarm signal(s) may be generated locally and within the vicinity of the access control reader 102. In one embodiment, the alarm signal(s) may be transmitted to another location within a building, to a network, to the system controller 104 (FIG. 1), wirelessly, and/or via Cloud computing.

Cloud computing is the on-demand availability of computer system resources, especially data storage (i.e., cloud storage) and computing power, without direct active management by the user. The term is generally used to describe data centers available to many users over the Internet. Large clouds, predominant today, often have functions distributed over multiple locations from central servers. If the connection to the user is relatively close, it may be designated an edge server.

Clouds may be limited to a single organization (i.e., enterprise clouds), or may be available to multiple organizations (i.e., public clouds). Cloud computing relies on sharing of resources to achieve coherence and economies of scale.

Figure 3A:
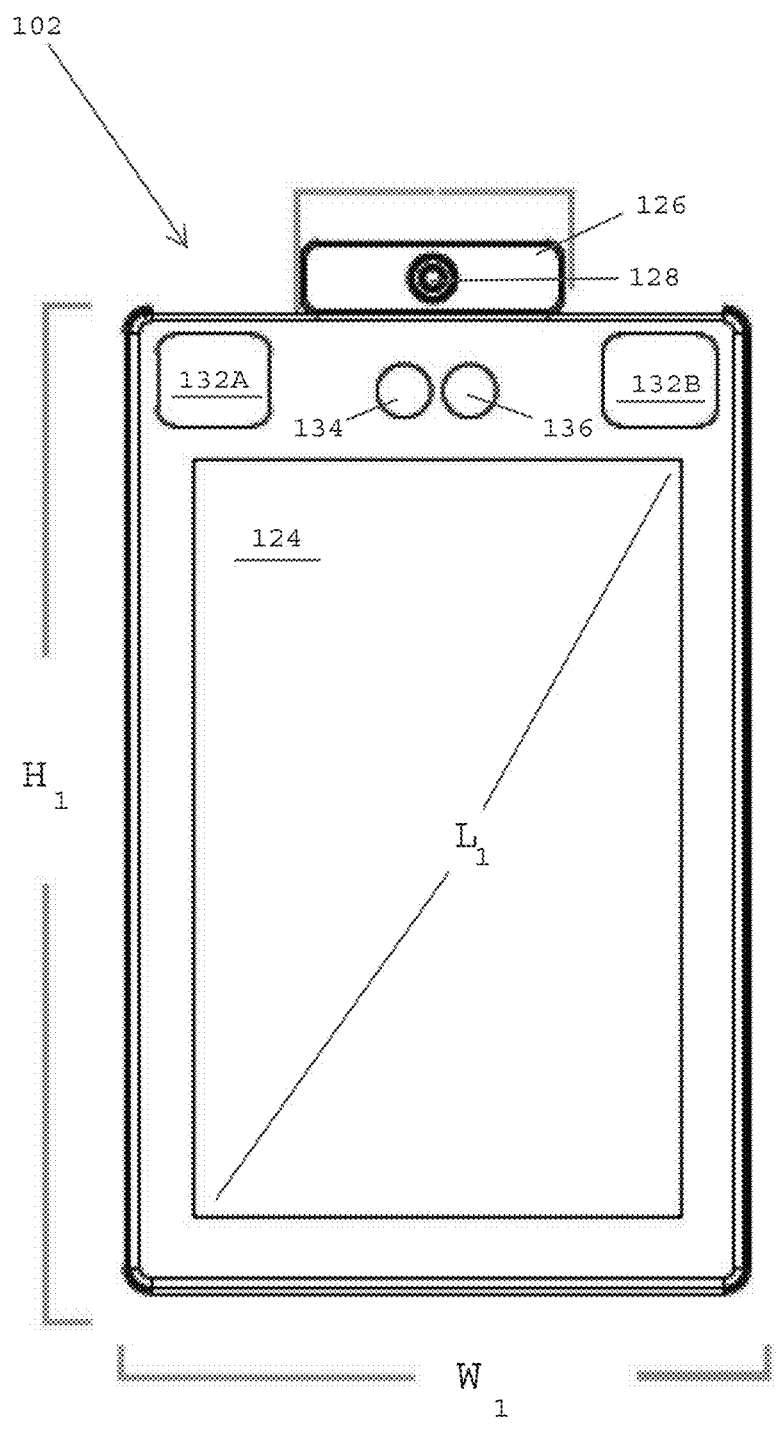
FIG. 3A is a front elevation view of an access control reader of an access control system, in accordance with one embodiment of the present patent application.

Referring to FIG. 3A, in one embodiment, the access control reader 102 preferably has a height $H_1$ of about 7-10 inches and more preferably about 8.9 inches and width $W_1$ of about 4-7 inches and more preferably about 5.6 inches. In one embodiment, the display screen 124 preferably has a diagonal display having a diagonal measurement $L_1$ of about 8 inches. In one embodiment, an access control reader may include a thermal sensor for obtaining skin temperature readings for employees and/or visitors.

In one embodiment, the access control reader 102 desirably includes the skin temperature sensor 126 having a thermal sensor 128 that is adapted for obtaining a skin temperature reading for an individual standing in front of the access control reader 102. In one embodiment, the skin temperature sensor 126 may have a width $W_2$ of about 2-4 inches and more preferably about 2.3 inches.

In one embodiment, the access control reader 102 preferably includes a first LED 132A and a second LED 132B that are adapted for generating light that is illuminated onto an individual standing in front of the access control reader. The access control reader 102 preferably includes the dual camera lens design having the first camera 134, which is adapted to obtain images within the visible spectrum and the second camera 136, which is adapted to obtain images within the infrared spectrum of light.

Figure 3B:
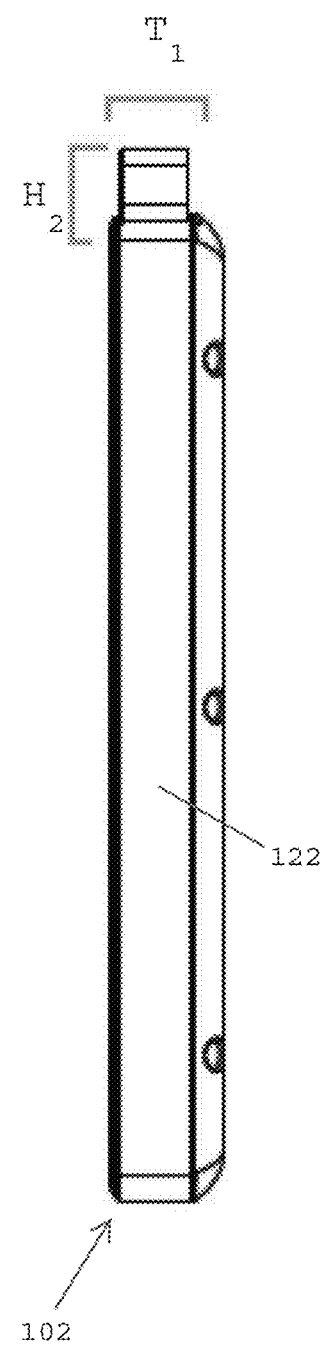
FIG. 3B is a side view of the access control reader shown in FIG. 3A.

Referring to FIG. 3B, in one embodiment, the access control reader 102 desirably includes the housing 122 that contains the display screen 124 (FIG. 3A) and electronic components for controlling and operating the access control reader 102. In one embodiment, the access control reader 102 may include many of the electronic components and application features that are found in a smart phone or electronic tablet. In one embodiment, the skin temperature sensor 126 is preferably mounted to an upper end of the housing 122. In one embodiment, the skin temperature sensor 126 has a height $H_2$ of about 0.65 inches and a thickness $T_1$ of about 1 inch.

Figure 4:
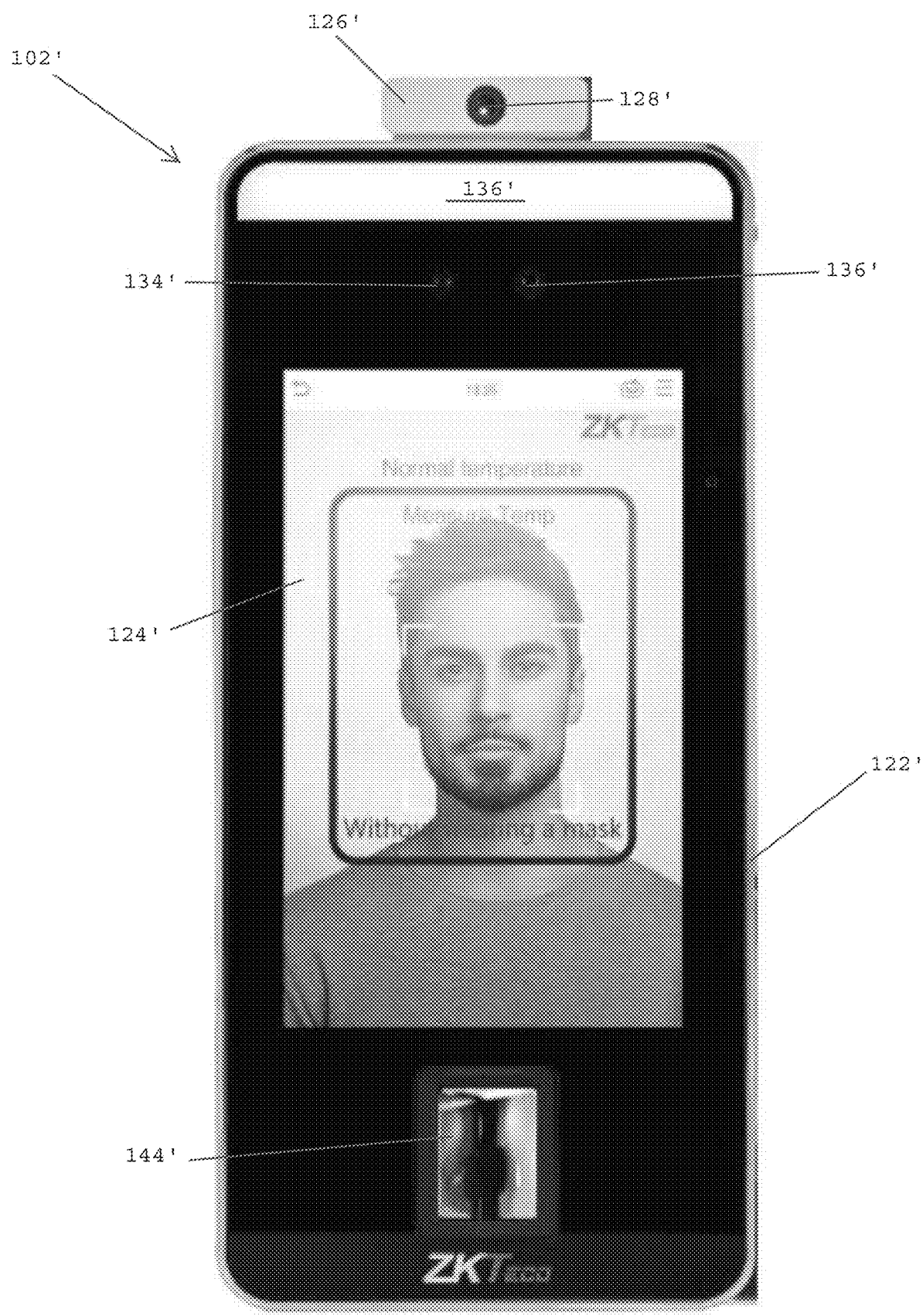
FIG. 4 is a perspective view of a front face of an access control reader of an access control system, in accordance with one embodiment of the present patent application.

Referring to FIG. 4, in one embodiment, an access control reader 102' preferably includes a housing 122' having a visual touchscreen display 124' that is adapted to display a picture or video image of an individual standing in front of the access controller reader 102'. The access control reader 102' preferably includes a skin temperature sensor 126' having a thermal sensor 128' that is utilized for obtaining temperature readings for an individual standing in front of the access control reader 102. In one embodiment, the skin temperature sensor 126' may utilize a thermographic camera for obtaining a thermal image of an individual standing in front of the access control reader 102'. In one embodiment, the skin temperature sensor 126' may include thermopile technology that is utilized for obtaining a skin temperature reading of an individual standing in front of the access control reader. In one embodiment, the access control reader 102' may include a fingerprint sensor and/or fingerprint scanner.

In one embodiment, the access control reader 102' preferably includes an LED light panel 132' that extends along an upper end of the housing 122'. The LED light panel 132' is preferably utilized for generating light that is illuminated onto an individual standing in front of the access control reader 102'.

In one embodiment, the access control reader 102' shown in FIG. 4 desirably includes the same technology, electronic components and features shown and described above for the embodiment of the access control reader 102 shown and described above in FIG. 2.

In one embodiment, the access control reader 102' preferably includes a fingerprint sensor 144' that may be utilized for obtaining a fingerprint reading of an individual interacting with the access control reader 102'. In one embodiment, prior to attempting to gain access to a controlled area, individual's may pre-register their respective fingerprints with the access control system 100 (FIG. 1). When interacting with the access control reader 102 during a user authentication protocol, an individual preferably positions his or her finger onto the fingerprint sensor 144', whereupon the individual's fingerprint is scanned by the fingerprint sensor 144'. The scanned fingerprint is compared to the pre-registered fingerprint that is on file for the individual attempting to gain access to a secure location via the access control reader 102'. In one embodiment, the access control reader 102' may store and match fingerprint images and/or biometric fingerprint templates.

In one embodiment, the access controller reader 102' preferably includes a dual camera lens design including a first camera 134' that is adapted to capture images within the visible light spectrum and second camera 136' that is adapted to obtain images within the infrared light spectrum.

Referring to FIG. 5A, in one embodiment, the access control reader 102' preferably has a height $H_3$ of about 6-9 inches and more preferably about 8 inches, and a width $W_3$ of about 3-5 inches and more preferably about 3.6 inches. In one embodiment, the access control reader 102' preferably has a display screen 124' having a diagonal display $L_2$ of about 6-8 inches and more preferably about 7 inches. The access control reader 102' desirably includes the skin temperature sensor 126' having the thermal sensor 128' for obtaining skin temperature readings for an individual that is standing in front of the access control reader. The detected skin temperature readings are analyzed to determine whether the individual has an acceptable skin temperature reading or an unacceptable skin temperature reading. In one embodiment, the display screens of access control readers may have diagonal lengths having various sizes including but not limited to 5, 7, 8, and 13 inches.

The access control reader 102' preferably includes the LED light panel 132' that is adapted for generating light that is illuminated onto an individual standing in front of the access control reader 102'. The access control reader 102' preferably includes the first camera 134' that is adapted to capture images within the visible light spectrum and the second camera 136' that is adapted to capture images within the infrared light spectrum. The access control reader 102' preferably includes the fingerprint sensor 144' that is adapted to scan fingerprints, whereupon the access control reader 102' compares a scanned fingerprint with a pre-recorded fingerprint for authenticating the identify of the individual attempting to gain access. In one embodiment, the access control reader may store and match fingerprint images and/or biometric fingerprint templates.

Referring to FIG. 5B, in one embodiment, the access control reader 102' preferably includes the housing 122' that contains the display screen 124' (FIG. 5A). In one embodiment, the skin temperature sensor 126' is mounted to the upper end of the housing 122'. In one embodiment, the skin temperature sensor 126' has a height $H_4$ of about 0.65 inches and a thickness $T_2$ of about 1 inch.

In one embodiment, the access control system 100 (FIG. 1) disclosed herein may use one or more rules that must be satisfied by an individual attempting to gain access into a controlled area. In one embodiment, a system operator may select and establish the rules that must be successfully satisfied by an individual before the individual is granted access into a controlled area. In one embodiment, the exact number of rules that must be satisfied may be modified to add additional rules and/or requirements or minimize the number of rules and/or requirements that must be satisfied for gaining access to a controlled are. For example, an access control system for a highly secure area (e.g., a nuclear power plant) may require more rules to be satisfied, and an access control system for a lower security area (e.g., a tire manufacturing facility) may require fewer rules to be satisfied.

Figure 6:
FIG. 6 is a schematic view of symbols that are associated with the rules of an access control system, in accordance with one embodiment of the present patent application.

Referring to FIG. 6, in one embodiment, various rules may be utilized for controlling access to a controlled area. The various rules may be associated with different visual icons. In one embodiment, an access control reader may have various sensors including human face recognition 146, palm recognition 148, skin temperature measurement 150, face mask detection 152, fingerprint recognition 154, QR and bar code recognition 156, and ID badge recognition 158.

In one embodiment, the access control system has a face recognition icon 146, which is associated with the rule that requires the access control reader 102 to confirm the facial identity of an individual prior to allowing the individual to access a controlled area. In one embodiment, an individual pre-registers an image (e.g., a picture) of his or her face with the access control system. In one embodiment, the access control reader 102 may store and match face images and/or biometric facial templates. During authentication, the image captured by the camera(s) of the access control reader are compared to the pre-registered image to confirm and authenticate the identity of the individual.

In one embodiment, the access control system may utilize a palm vein pattern recognition icon 148, which is associated with the rule requiring palm vein pattern recognition prior to allowing access to a controlled area. In one embodiment, the access control reader 102 may store and match vein pattern images and/or biometric vein pattern templates.

In one embodiment, the access control system may utilize a temperature reading icon 150, which is associated with the rule requiring an individual to have an acceptable skin temperature reading prior to being authorized access into a controlled area.

In one embodiment, the access control system may utilize a mask icon 152, which is associated with the rule requiring the access control reader to confirm whether an individual is wearing a protective mask prior to being authorized access into a controlled area.

In one embodiment, the access control system may include a fingerprint icon 154, which is associated with the rule requiring an individual's scanned fingerprint to match his or her pre-registered fingerprint prior to being authorized access into a controlled area. In one embodiment, the access control reader 102 may store and match fingerprint images and/or biometric fingerprint templates.

In one embodiment, the access control system may utilize an RFID icon 156, which is associated with the rule requiring an access control reader to detect the presence of an RFID chip prior to authorizing an individual to access to a controlled area.

In one embodiment, the system may utilize a proximity card icon 158, which is associated with the rule requiring a proximity card to be detected and authenticated prior to authorizing an individual to access a controlled area.

In other embodiments, the system may require a user to punch in a number such as a Personal Identification Number (e.g., a PIN code). In one embodiment, the system may require the user to display a pre-assigned QR code that has been sent to a user's phone, electronic device and/or computer via text message or e-mail. In one embodiment, the access control reader will preferably scan the OR code to determine whether an individual is authorized access into a secure or controlled area. In other embodiments, the system may authenticate using barcodes, magnetic strips, Bluetooth technology, near field communication (NFC), ultrawide band (UWB), ultrahigh frequency (UHF), Zigbee, Zwave, and artificial intelligence voice responders including Amazon Alexa, Apple Siri, and Google Assistant.

Figure 7:
FIG. 7 shows a perspective view of a system controller of an access control and visitor management system, in accordance with one embodiment of the present patent application.

Referring to FIG. 7, in one embodiment, a host uses a system controller 104 of an access control system 100 to schedule an appointment for a visitor. In one embodiment, the host transmits a QR code to the visitor via a text message or an e-mail. The QR code may be displayed on a display screen of an electronic device (e.g., a smart phone) or may be printed on paper for being scanned by a QR code reader of an access control reader. In one embodiment, the system controller 104 may interface with the access control reader through either a computer or a mobile device.

Figure 8:
FIG. 8 shows a stage of using an access control system and visitor management system, in accordance with one embodiment of the present patent application.

Referring to FIG. 8, in one embodiment, a visitor V with a scheduled appointment walks toward a building having a controlled area. In one embodiment the access control system may perform face recognition and is IP68 and IK04-rated. As a result, users may be authenticated outside prior to entering the building and unlock the building's front door entrance if they have the necessary access rights.

Figure 9:
FIG. 9 shows a stage of using an access control system, in accordance with one embodiment of the present patent application.

Referring to FIG. 9, in one embodiment, prior to entering the building, the visitor V dons a protective mask 160

Figure 10:
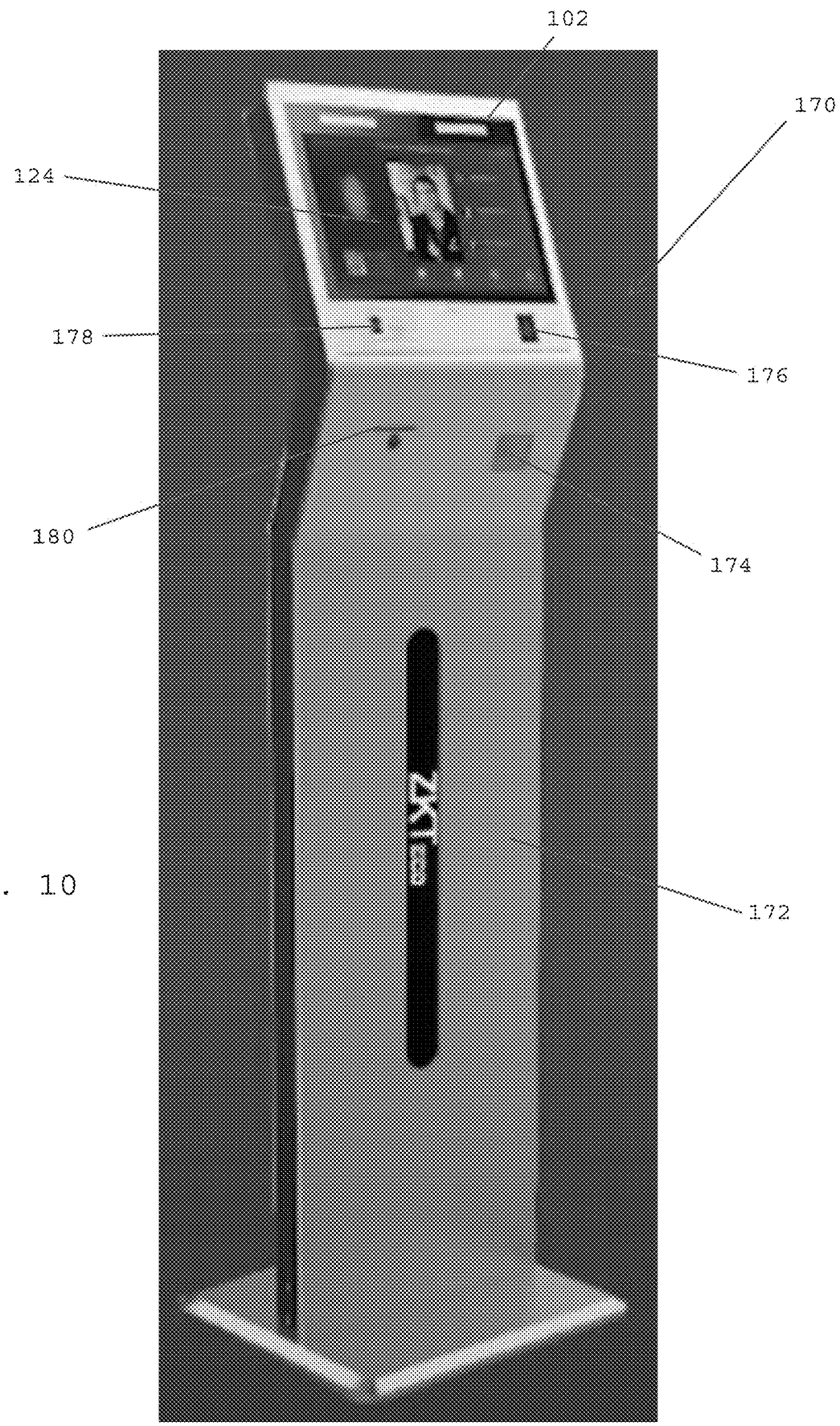
FIG. 10 is a perspective view of a visitor management kiosk of an access control system, in accordance with one embodiment of the present patent application.

Referring to FIG. 10, in one embodiment, an access control system 100 (FIG. 1) may include a visitor management kiosk 170 having a stand 172 and an access control reader 102 mounted to an upper end of the stand 172. The access control reader 102 preferably includes all the technology previously disclosed herein. In one embodiment, the visitor management kiosk 170 preferably includes a QR code scanner 174 that may be utilized for scanning a QR code that has been previously sent to an individual attempting to gain access into a controlled area.

In one embodiment, the visitor management kiosk 170 desirably includes a fingerprint reader 176 that may be utilized for obtaining a fingerprint reading of an individual attempting to gain access to a controlled area. In one embodiment, the scanned fingerprint is preferably compared to a pre-registered fingerprint to confirm the identity of an individual seeking access. In one embodiment, the visitor management kiosk may store and match fingerprint images and/or biometric fingerprint templates.

In one embodiment, the visitor management kiosk 170 desirably includes an RFID card reader 178 that is adapted to validate an RFID card held by the individual attempting to gain access to a controlled area. The visitor management kiosk 170 may read any type of RFID technology including generic 125 kHz, HID 125 kHz/prox, HID iClass, 13.56 MHz, Legic, AWID, multi-frequency, etc.

In one embodiment, the visitor management kiosk 170 preferably includes a printer and a ticket slot 180 that is used for dispensing an entry badge or a ticket to an individual attempting to gain access to a controlled area. In one embodiment, after an individual has been fully authenticated, the visitor management kiosk 170 will desirably print an entry badge or ticket, which may then be dispensed via the ticket slot 180, whereupon the entry badge or ticket may be grasped by the individual attempting to gain access to the controlled area. The printed badge may contain a QR code, which may be used to access a physical barrier having a QR code reader attached. The printed badge may also simply print an access code which can be visually validated by onsite security personnel.

In one embodiment, the access control reader 102 preferably includes a display screen 124. The display screen 124 may incorporate touch screen technology and may allow the user to be interactive with the visitor management kiosk 170. The access control reader preferably includes the electronic components and features disclosed in the other embodiments of the present patent application.

In one embodiment, the visitor management kiosk 170 may include a health check questionnaire protocol that is displayed on the display screen 124. In one embodiment, an individual attempting to gain access to a controlled area is required to successfully complete and answer the health check questionnaire. In one embodiment, an individual attempting to gain access to a controlled area must first pass the health check review prior to being authorized to gain access to the controlled area. The health check questionnaire may be displayed on the visitor's mobile phone or the kiosk's touchscreen. In one embodiment, the touchscreen may be connected to external motion sensors so that visitors and employees may respond to the health check questions without touching the kiosk.

In one embodiment, the health check questionnaire is user-definable, as is the kiosk's background display, wallpaper, and "thank you" e-mail/text messages, which may be automatically transmitted to visitors and employees after they have successfully passed the authentication and health screening check.

In one embodiment, the visitor management kiosk 170 is preferably in communication with a system controller 104 (FIG. 1) that is adapted to monitor the status of the authentication check for the individual attempting to gain access to the controlled area. If the individual fails any stage of the authentication check, the visitor management kiosk 170 will generate and/or transmit a signal to the central controller for generating an alert or an alarm signal (e.g., flashing light; a siren).

In one embodiment, if an individual successfully satisfies all the rules of the access control system, the visitor management kiosk 170 will generate a signal that may be transmitted to a host, which is designated as a person that is tasked with greeting the individual once they pass into the controlled area. The visitor access kiosk 170 may also dispense an access ticket or badge, and may also unlock one or more components (e.g., a door; a turnstile) for providing access to a controlled area.

Figure 11:
FIG. 11 is a perspective view of an upper end of a visitor management kiosk of an access control system and a thermal sensor atop the kiosk, in accordance with one embodiment of the present patent application.
Figure 12:
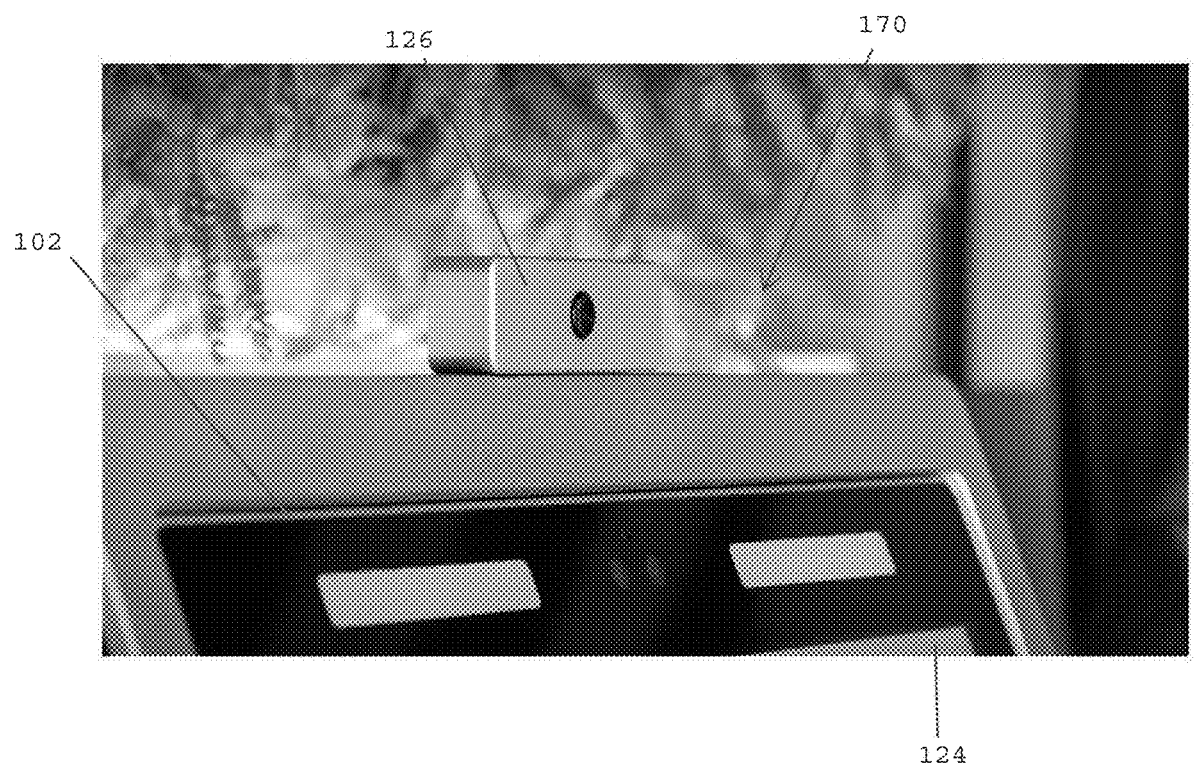
FIG. 12 is a perspective view of an upper end of the visitor management kiosk of FIG. 11 including the thermal sensor, in accordance with one embodiment of the present patent application.

Referring to FIGS. 11 and 12, in one embodiment, a visitor management kiosk 170 of an access control system is located inside an outer lobby of a secure facility. The visitor management kiosk 170 has an access control reader 102 with a display screen 124 having touch-screen technology. A skin temperature sensor 126 is mounted atop the visitor management kiosk 170.

Figure 13:
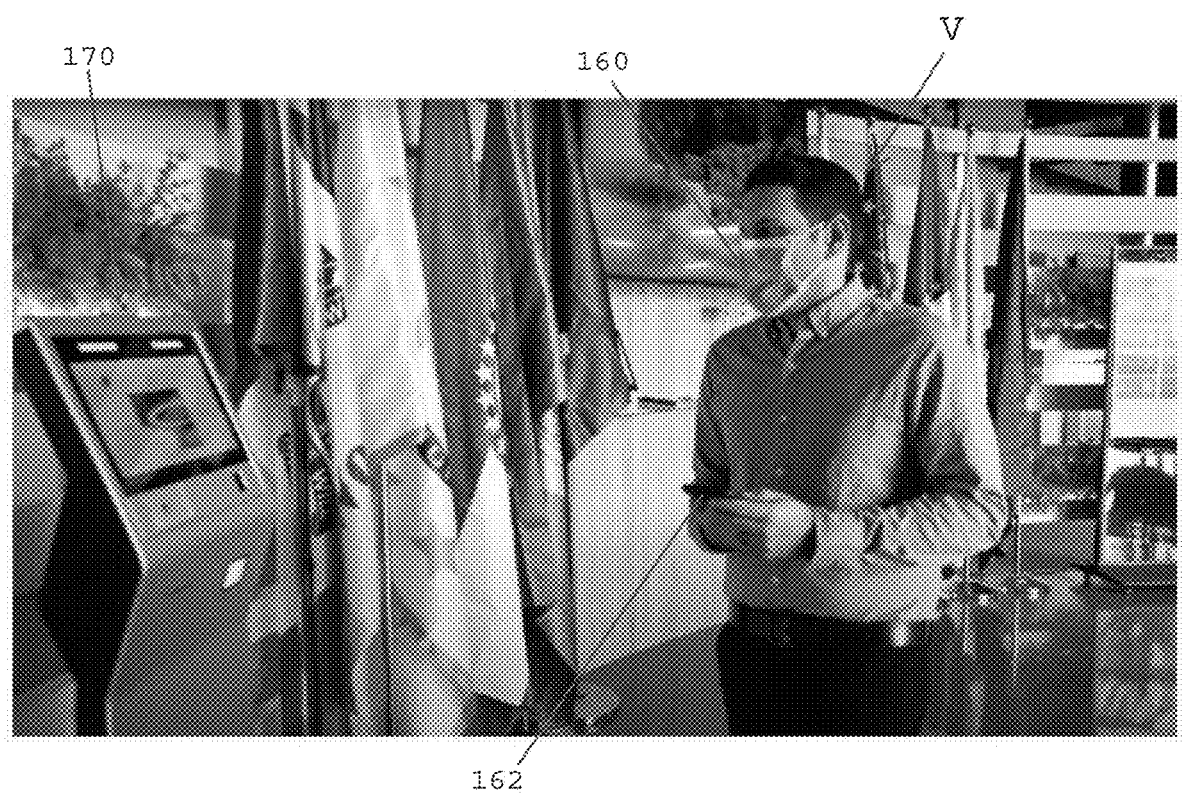
FIG. 13 shows a first stage of a method of using a visitor management kiosk of an access control system including a thermal sensor, in accordance with one embodiment of the present patent application.

Referring to FIG. 13, in one embodiment, the visitor V approaches the visitor management kiosk 170. The visitor V is wearing a protective mask 160. The visitor V is carrying a smart phone 162 that displays a QR code on a display screen of the smart phone.

Figure 14:
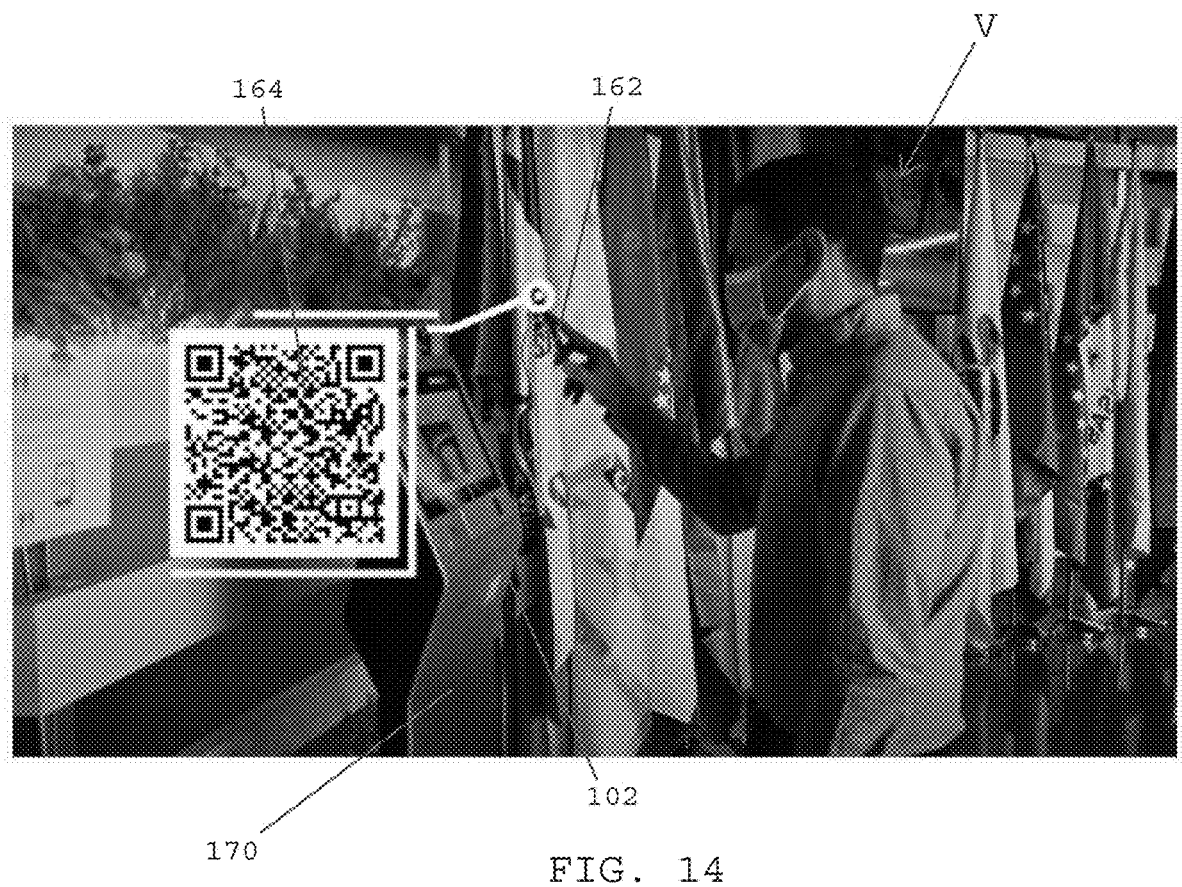
FIG. 14 shows a second stage of a method of using the visitor management kiosk of an access control system, in accordance with one embodiment of the present patent application.

Referring to FIG. 14, in one embodiment, the visitor V presents the OR code 164 that is displayed on the smart phone 162 to the access control reader 102 of the visitor management kiosk 170, whereupon the access control reader 102 confirms that the QR code 164 is valid and has been assigned to the visitor V. In one embodiment, the visitor management kiosk 170 may also be capable of reading bar codes, drivers' licenses, and other forms of printed identification.

Figure 15:
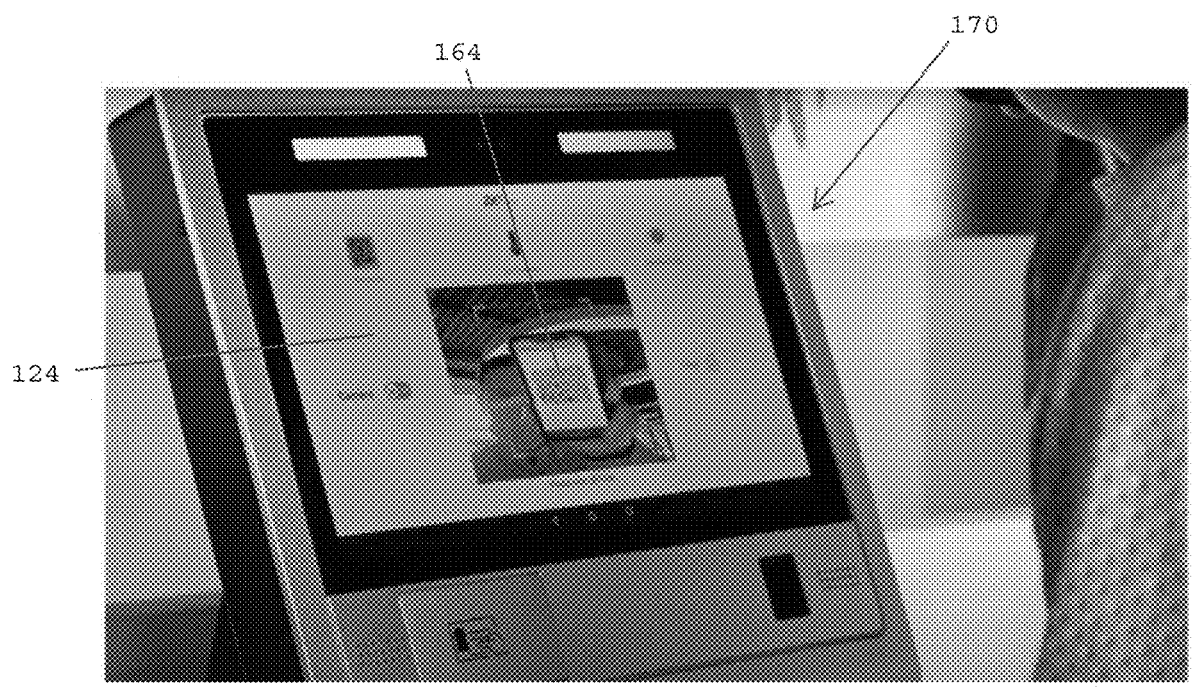
FIG. 15 shows a third stage of a method of using the visitor management kiosk of an access control system, in accordance with one embodiment of the present patent application.

Referring to FIG. 15, in one embodiment, the QR code 164 that has been scanned by the visitor management kiosk 170 is displayed on the display screen 124 of the access control reader 102 of the visitor management kiosk 170. In one embodiment, the visitor management kiosk may have a separate QR code scanner that is in communication with the kiosk.

Figure 16:
FIG. 16 shows a fourth stage of a method of using the visitor management kiosk of an access control system, in accordance with one embodiment of the present patent application.
Figure 17:
FIG. 17 shows a fifth stage of a method of using the visitor management kiosk of an access control system, in accordance with one embodiment of the present patent application.

Referring to FIGS. 16 and 17, in one embodiment, after the QR code has been authenticated, the visitor V preferably stands in front of the cameras 134, 136 (FIGS. 2 and 3A) of the access control reader 102 for capturing an image of the visitor's face and comparing the captured image with the pre-registered picture of the visitor V. The captured image of the visitor's face is displayed on the display screen 124 of the access control reader 102. The access control reader 102 also confirms that the visitor is wearing a protective mask 160. In one embodiment, the visitor management kiosk may be capable of recognizing registered users with and without wearing a protective mask.

In one embodiment, the skin temperature sensor 126 (FIG. 16) obtains a skin temperature reading for the visitor V. If the skin temperature reading is acceptable, the access control reader preferably displays the message "Normal Temperature" on the display screen 124. The "Normal Temperature" message may be displayed in green. If the skin temperature reading is unacceptable, the access control reader preferably displays the message "Above Normal Temperature" on the display screen 124. The "Above Normal Temperature" message may be displayed in red.

Figure 18:
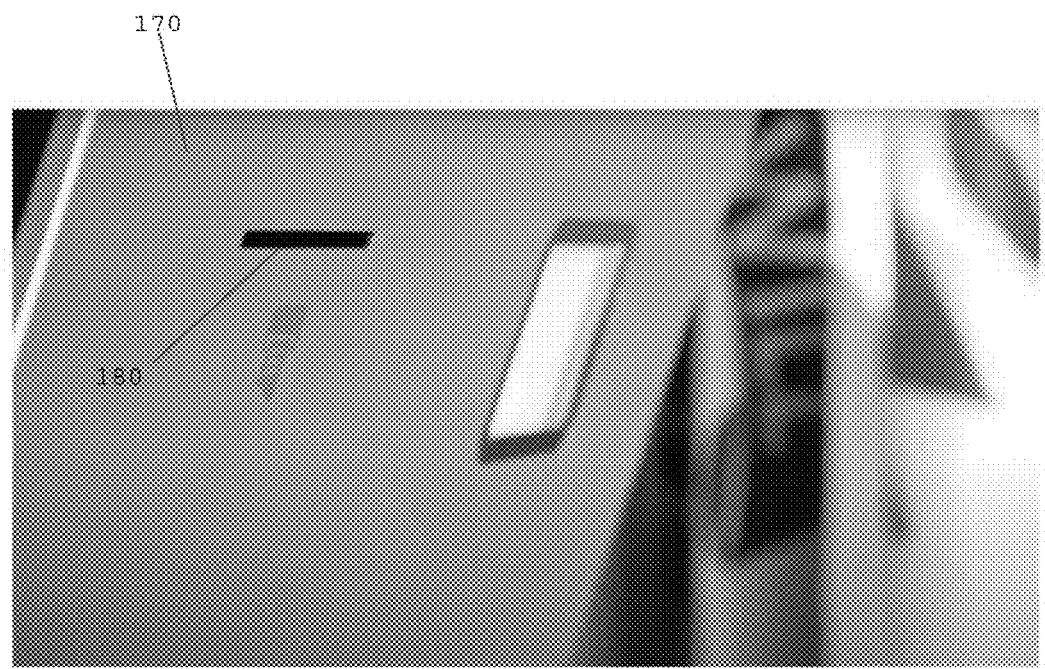
FIG. 18 shows a sixth stage of a method of using the visitor management kiosk of an access control system, in accordance with one embodiment of the present patent application.

Referring to FIG. 18, after the visitor V has successfully satisfied the established rules of the access control system for gaining access to a controlled area (e.g., QR code match; user authenticated; wearing protective mask; acceptable skin temperature), the visitor management kiosk 170 may print and dispense a ticket or badge to the visitor via the ticket slot 180. In one embodiment, the visitor management kiosk preferably has an integrated internal printer (not shown in FIG. 18), which is adapted to print admittance tickets.

Figure 19:
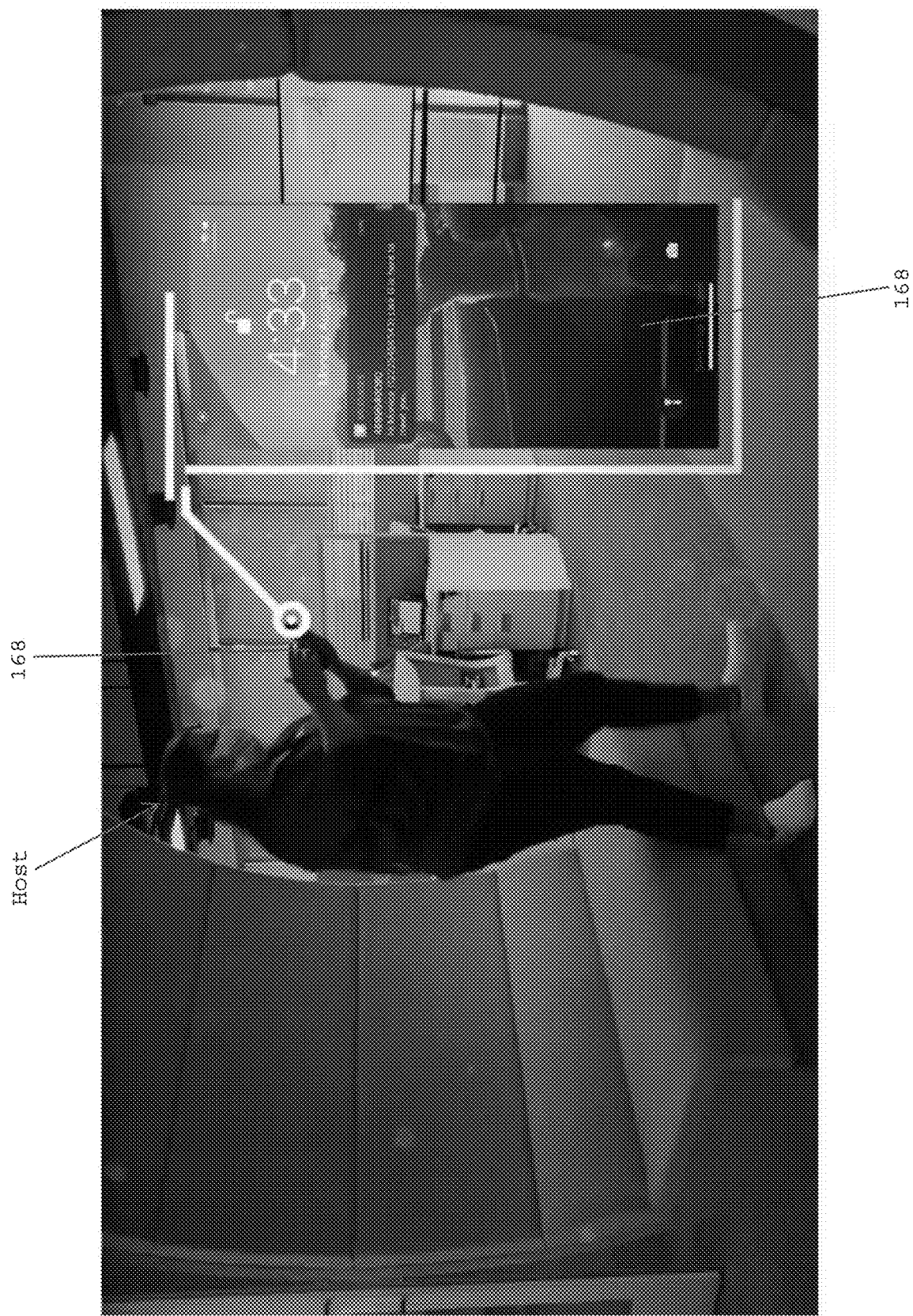
FIG. 19 shows a stage of using an access control system during which a host is notified that a visitor has been successfully authenticated by the visitor management kiosk of an access control system, in accordance with one embodiment of the present patent application.

Referring to FIG. 19, in one embodiment, when the visitor V (FIG. 16) has successfully satisfied the rules of the access control system and has been issued an access ticket by the visitor management kiosk 170 (FIG. 16), the access control reader of the visitor management kiosk preferably generates a notification message that may be sent to an electronic device 168 (e.g., a smart phone) of the host. The host may proceed to an inner lobby area to greet the visitor V.

Figure 20:
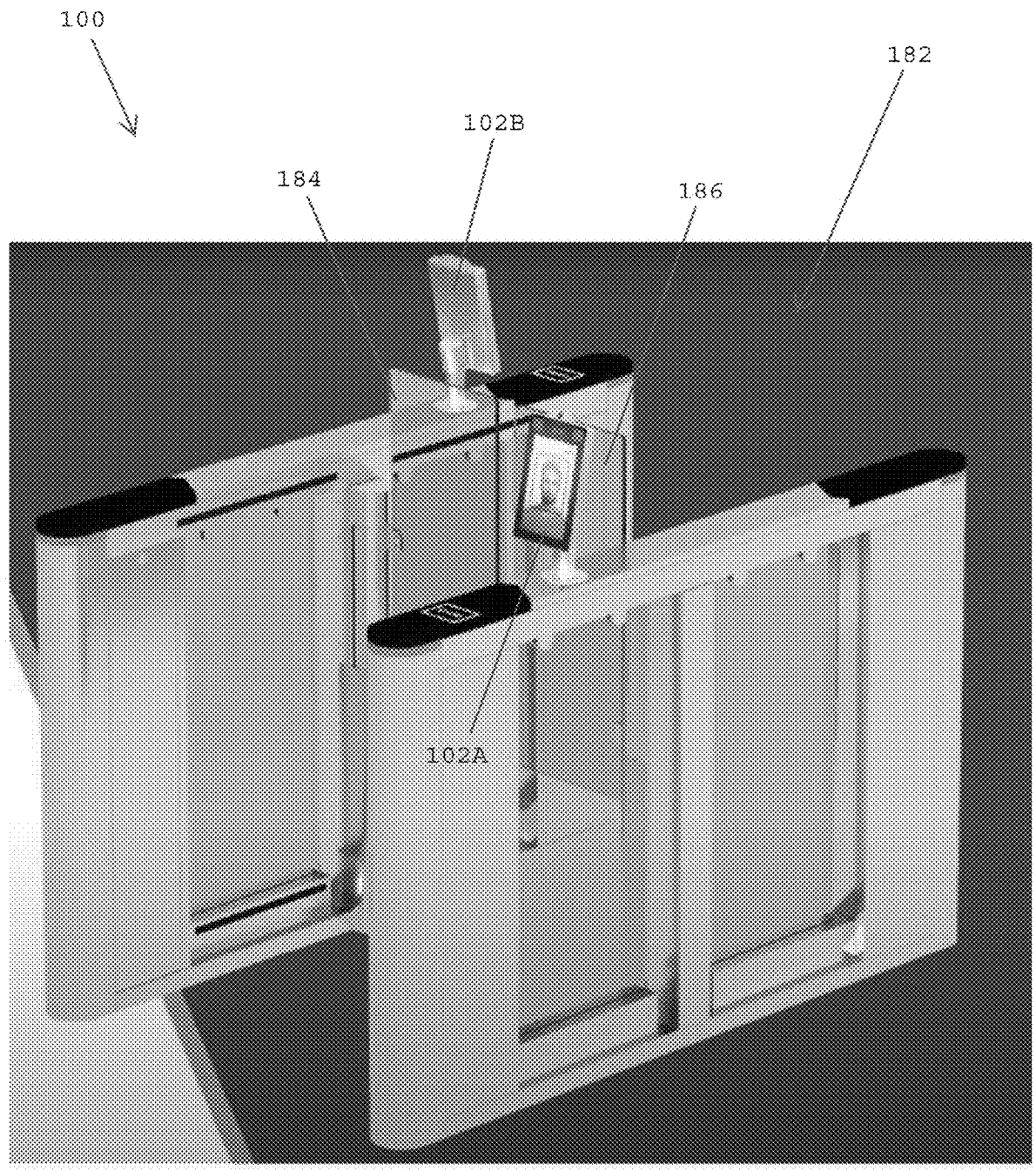
FIG. 20 is a perspective view of a turnstile of an access control system, the turnstile having access control readers mounted thereon, in accordance with one embodiment of the present patent application.

Referring to FIG. 20, in one embodiment, an access control system 100 may include a turnstile 182 having opposing gates 184, 186 that open and close for controlling access to a controlled area. In one embodiment, the turnstile may be a stand-alone system. In one embodiment, the turnstile may be used in conjunction with a visitor management kiosk and/or a walkthrough metal detector. In one embodiment, a first access control reader 102A is configured for monitoring and authenticating individuals attempting to gain access into a controlled area. In one embodiment, a second access control reader 102A is configured for monitoring and authenticating individuals exit the controlled area. The first and second access control readers 102A, 102B are preferably linked with a system controller of the access control system for establishing the rules for when individuals may be granted access into the controlled area and for maintaining a real-time room occupancy level. In one embodiment, when the system controller determines that the controlled area's room occupancy level has reached maximum allowance, the system controller preferably instructs the first access control reader 102A to keep the turnstile locked until the room occupancy level drops below the maximum allowance. In one embodiment, authorized individuals may resume passing through the turnstile and entering the controlled area if the room occupancy level remains below maximum allowance.

Figure 21:
FIG. 21 is a front side view of a turnstile of an access control system, in accordance with one embodiment of the present patent application.

Referring to FIG. 21, in one embodiment, the turnstile 182 limits access to a controlled area that lies beyond the closed gates of the turnstile. An access control reader 102 is configured to be at head height level on the entrance side of the turnstile 182.

Figure 22:
FIG. 22 is a perspective view of an access control reader that is linked with the turnstile shown in FIG. 21, in accordance with one embodiment of the present patent application.

Referring to FIG. 22, in one embodiment, the access control reader 102 associated with the turnstile 182 (FIG. 21) preferably includes a housing 122 that contains a display screen 124 (e.g., video screen) that has touch-screen technology.

In one embodiment, the access control reader 102 preferably includes a skin temperature sensor 126 including a thermal sensor 128 that may be utilized for detecting the skin temperature of an individual interacting with the access control reader. In one embodiment, the skin temperature sensor 126 may incorporate thermographic imaging technology or thermopile technology for obtaining skin temperature readings of individuals who stand in front of the skin temperature sensor 126. In one embodiment, the display screen 124 of the access control reader 102 includes a thermal image section 130 that shows a thermal image of the individual standing in front of the access control reader.

In one embodiment, the access control reader 102 preferably includes a first light emitting diode (LED) 132A and a second LED 132B that are utilized for generating light, which is illuminated onto an individual standing in front of the access control reader.

In one embodiment, the access control reader 102 preferably includes a dual camera lens design having a first camera 134 that detects light within the visible light spectrum and a second camera 136 that detects light within the infrared spectrum. In one embodiment, the infrared camera 136 is preferably utilized for obtaining infrared images of an individual, which are used by integrated biometric (e.g., face, palm, etc.) recognition technology to confirm that the person standing in front of the access control reader is the same person who has pre-registered his or her credentials with the access control system.

In one embodiment, when an individual seeking to be authenticated stands in front of the access control reader 102, the skin temperature sensor 126 is utilized for obtaining a temperature reading for the individual. The skin temperature reading may be displayed within a temperature reading section of the visual display 124.

Figure 23:
FIG. 23 shows a first stage of a method of using a turnstile of an access control system, in accordance with one embodiment of the present patent application.
Figure 24:
FIG. 24 shows a second stage of a method of using the turnstile of an access control system, in accordance with one embodiment of the present patent application.

Referring to FIGS. 23 and 24, in one embodiment, the visitor V approaches the front face of the access control reader 102 that is mounted atop the turnstile 182. The visitor V stands in front of the access control reader 102 so that the access control reader may capture an image of the visitor's face or palm to confirm the identity of the visitor, to obtain a skin temperature reading, and to determine if the visitor V is wearing a protective mask 160. The LED's 132A, 132B may generate light that is illuminated onto the face of the visitor V.

Figure 25:
FIG. 25 shows a third stage of a method of using the turnstile of an access control system, in accordance with one embodiment of the present patent application.

Referring to FIG. 25, in one embodiment, the image of the visitor's face or palm that is captured by one or more cameras of the access control reader 102 is shown on the display screen 124 of the access control reader 102. The captured image is compared to the pre-registered image 142.

The visitor's recorded skin temperature is displayed in the skin temperature section 138 of the display screen 124. The visitor's recorded skin temperature and the message "Normal Temperature" may be displayed in green on the display screen 124.

Figure 26:
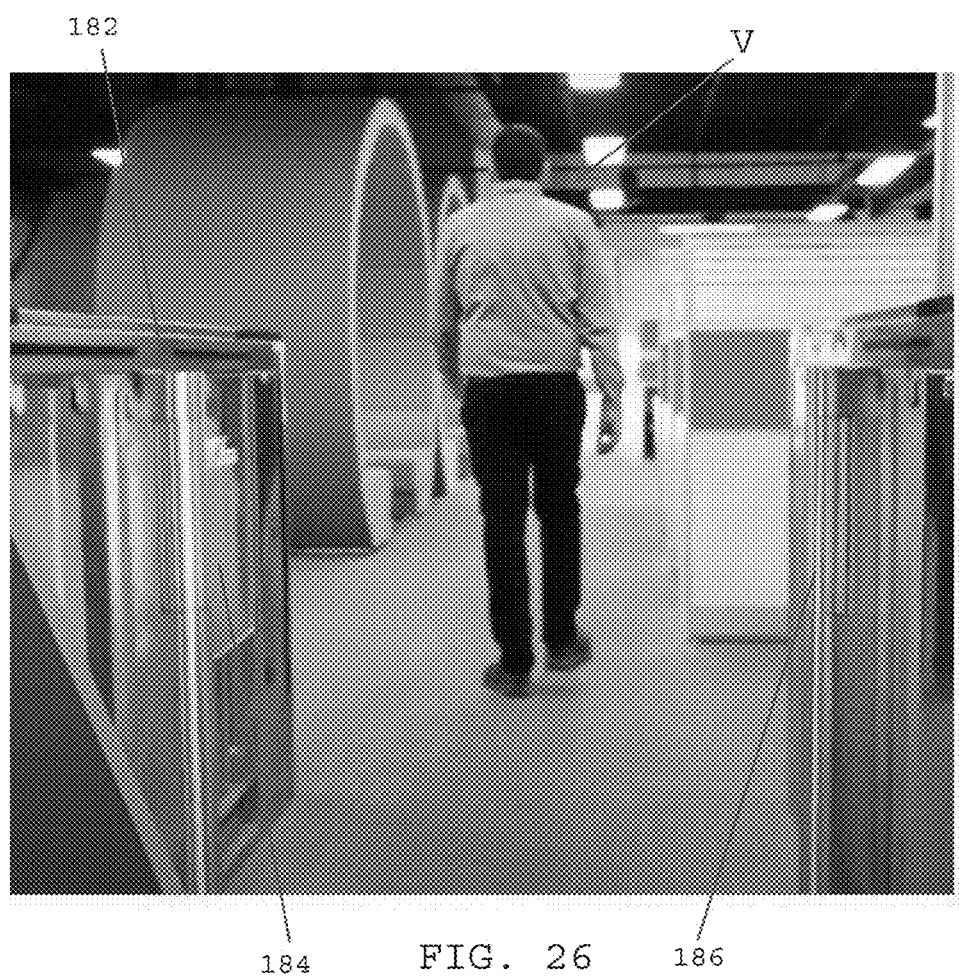
FIG. 26 shows a fourth stage of a method of using the turnstile of an access control system, in accordance with one embodiment of the present patent application.

Referring to FIG. 26, in one embodiment, after the visitor V has been properly authenticated by the access control reader and after the visitor has satisfied the rules of the access control system (e.g., acceptable temperature; wearing a mask), the gates 184, 186 of the turnstile 182 will open to allow the visitor V to pass through the turnstile and proceed into a controlled area that lies beyond the turnstile 182.

Figure 27:
FIG. 27 shows an access control reader of an access control system, and a support base adapted for positioning the access control reader atop a table, in accordance with one embodiment of the present patent application.

Referring to FIG. 27, in one embodiment, an access control reader 102 may be secured atop a table-top stand 190.

Figure 28:
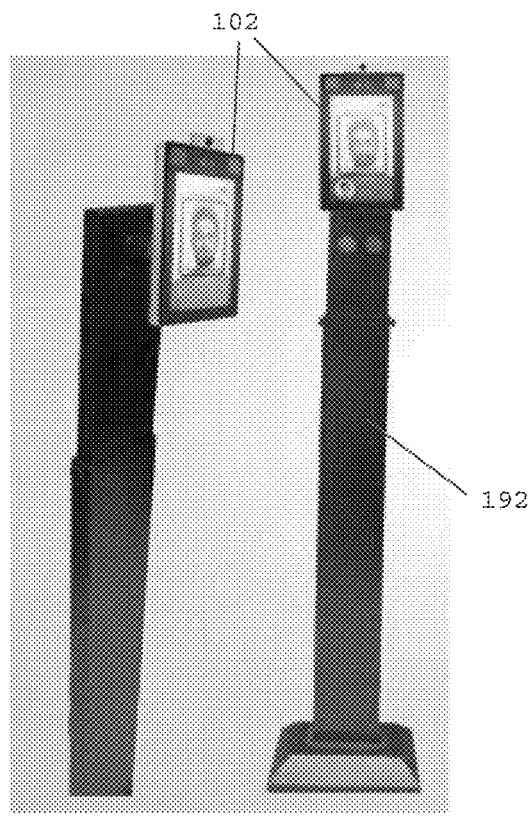
FIG. 28 shows a perspective view of access control readers mounted atop stands, in accordance with one embodiment of the present patent application.

Referring to FIG. 28, in one embodiment, an access control reader 102 may be mounted atop an elongated floor stand 192. In one embodiment, the stand may have a green light that is illuminated when a visitor has been authenticated and has satisfied all the rules established for the access control system. When the green light illuminates, the visitor may proceed toward the controlled area. In one embodiment, the stand may have a red light that is illuminated when a visitor has not satisfied all the rules established for the access control system. When the red-light illuminates, the visitor has been denied access and may not proceed toward the controlled area.

Figure 29:
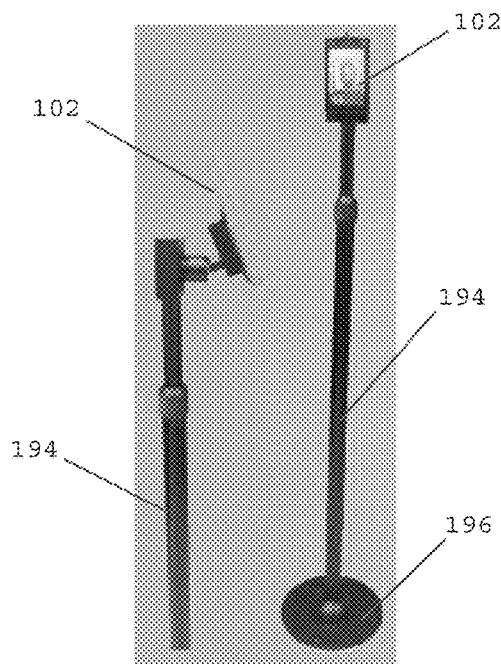
FIG. 29 shows a perspective view of access control readers mounted atop poles, in accordance with one embodiment of the present patent application.

Referring to FIG. 29, in one embodiment, an access control reader 102 may be mounted atop an elongated pole 194 having a floor pedestal 196.

Figure 30:
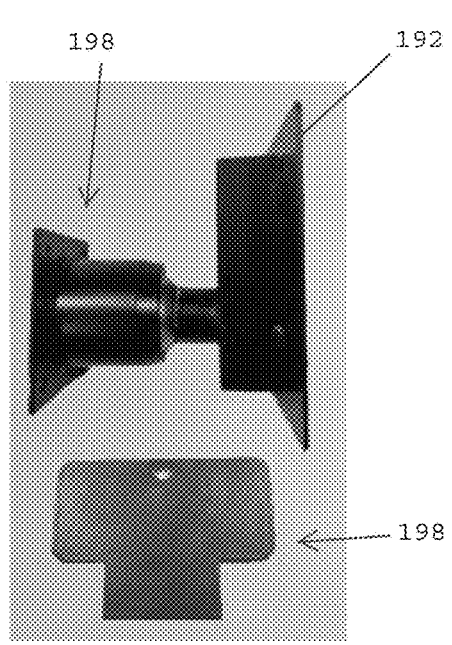
FIG. 30 shows an access control reader and a wall mounting bracket, in accordance with one embodiment of the present patent application.

Referring to FIG. 30, in one embodiment, an access control reader 102 may be mounted to a wall using wall-mounting components 198.

Figure 31:
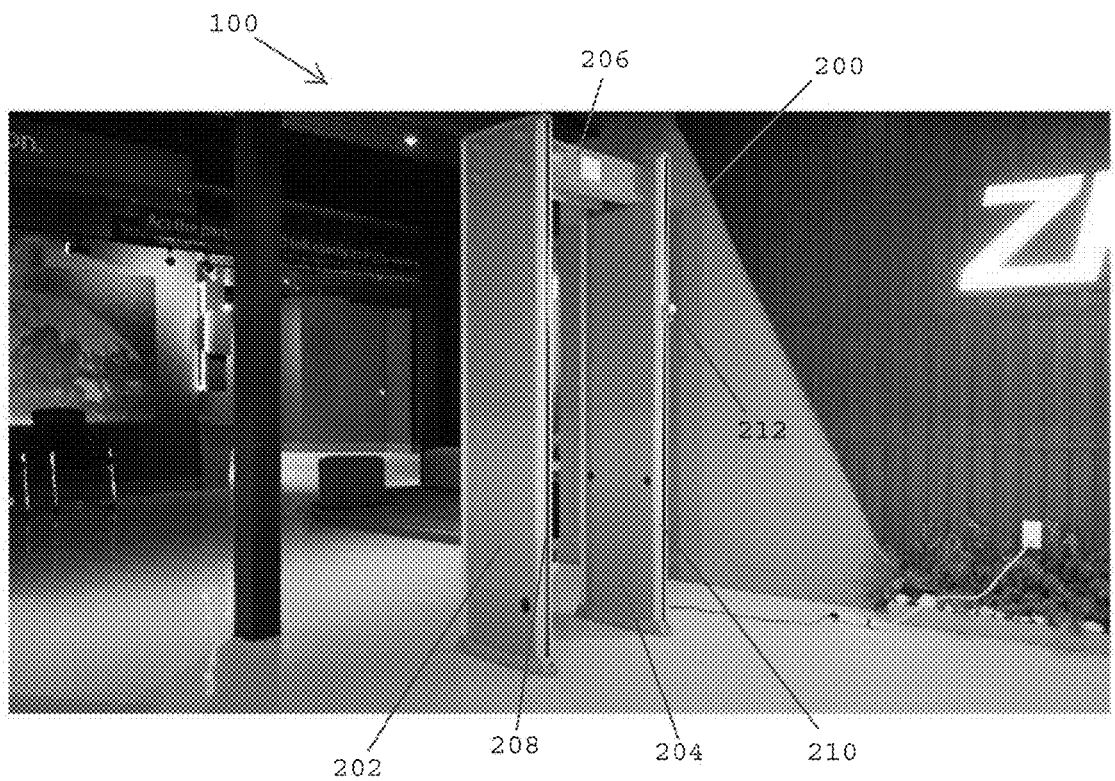
FIG. 31 is a perspective view of a walkthrough metal detector station of an access control system, the metal detector having a skin temperature monitor, in accordance with one embodiment of the present patent application.

Referring to FIG. 31, in one embodiment, an access control system 100 may include a walkthrough metal detector 200 that is adapted to detect the presence of metal on individuals that pass through the walkthrough metal detector. In one embodiment, the walkthrough metal detector 200 preferably includes a first vertically extending panel 202, a second vertically extending panel 204 that is spaced away from the first vertically extending panel 202, and a horizontally extending panel 206 that interconnects the upper ends of the first and second vertically extending panels 202, 204. In one embodiment, the horizontally extending panel 206 serves as a metal detector control module. In one embodiment, the control module preferably displays each visitor's skin temperature. In one embodiment, the control module also desirably displays the tallied number of visitors walking through the metal detector 200 and the tallied number of alarms. The resulting data is preferably stored in a computer networked with the walkthrough metal detector 200. The data may be used for subsequent auditing reporting purposes. In one embodiment, the walkthrough metal detector 200 may also be fitted with an optical or mechanical barrier which allows the walkthrough metal detector 200 to also act as a turnstile.

Figure 32:
FIG. 32 shows a first stage of a method of using a walkthrough metal detector of an access control system, in accordance with one embodiment of the present patent application.

Referring to FIGS. 31 and 32, in one embodiment, the walkthrough metal detector 200 preferably includes a first LED light bank 208 that extends vertically along a front face of the first vertically extending panel 202 and a second LED light bank 210 that extends vertically along a front face of the second vertically extending panel 204. As will be described in more detail herein, the LED light banks may illuminate to alert tending security personnel that an individual attempting to pass through the walkthrough metal detector has an unacceptable skin temperature or is carrying metal on their person. In one embodiment, the first LED light bank 208 will illuminate in instances in which a metal object is detected on a left side of an individual passing through the walkthrough metal detector 200, which helps tending security personnel to quickly locate a metal object on the individual by wanding the individual with a handheld metal detector. In one embodiment, the second LED light bank 2210 will illuminate in instances in which a metal object is detected on a right side of an individual passing through the walkthrough metal detector 200, which again helps security personnel to quickly locate a metal object on the individual.

In one embodiment, the walkthrough metal detector 200 preferably includes a skin temperature sensor 212 that is mounted on the front face of the second vertically extending panel 204, which is adapted to obtain a skin temperature reading of an individual that seeks to pass through the walkthrough metal detector 200. Single and multiple skin temperature sensors 212 may be mounted on either vertical panel at varying heights, to ensure all types of individuals can be effectively and expeditiously scanned for unacceptable skin temperature.

In one embodiment, upper ends of the first and second LED light banks 208 210 will illuminate in instances in which an unacceptable skin temperature reading has been detected for an individual seeking to pass through the walkthrough metal detector 200.

Figure 33:
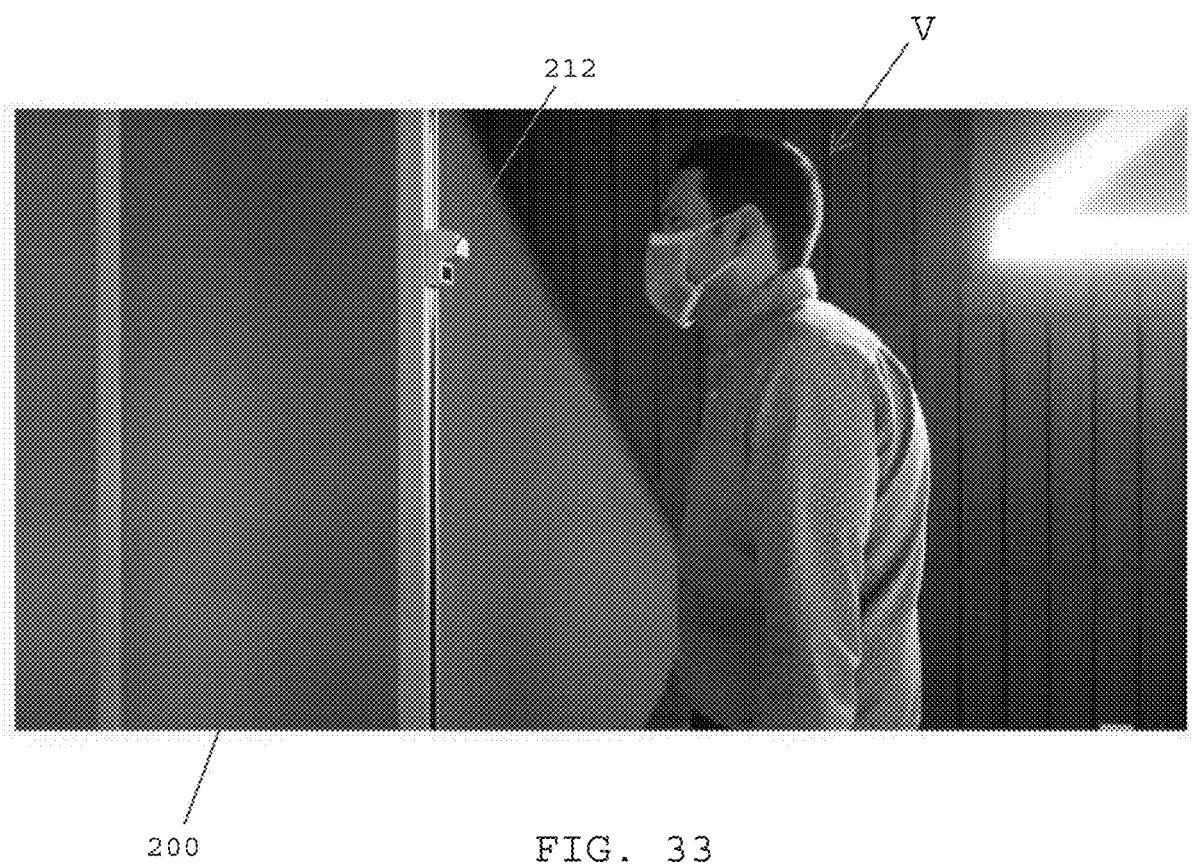
FIG. 33 shows a second stage of a method of using the walkthrough metal detector of an access control system, in accordance with one embodiment of the present patent application.
Figure 34:
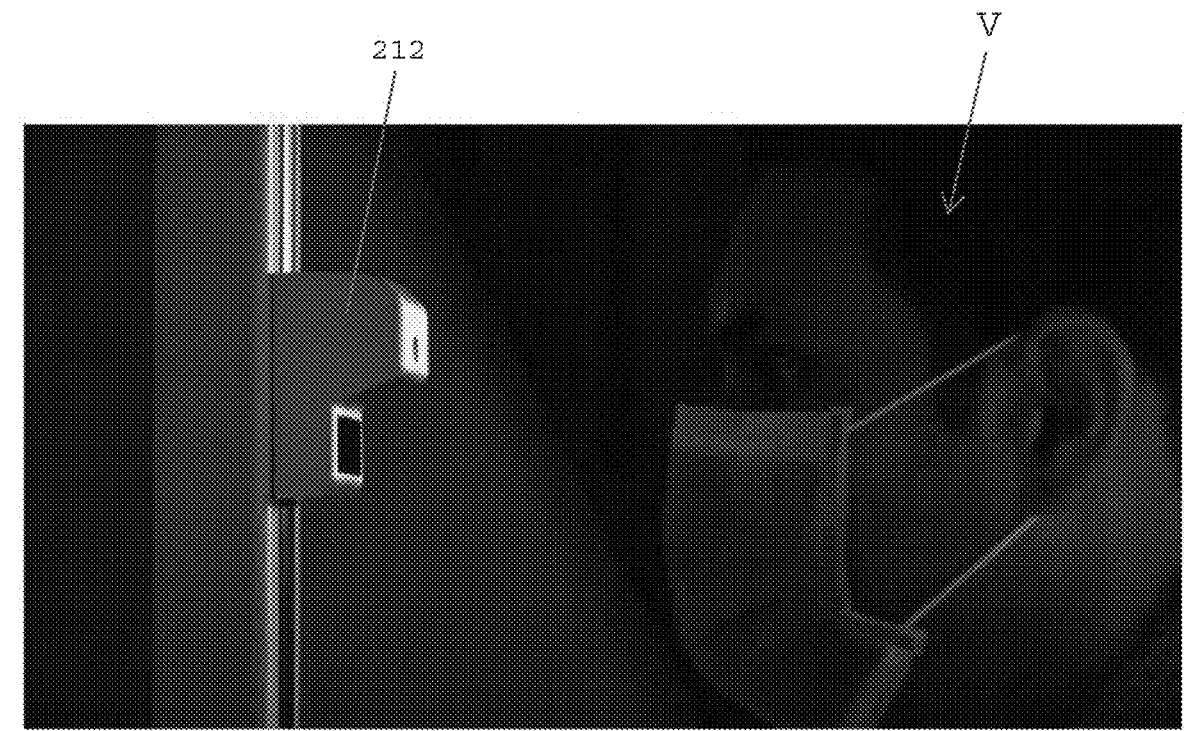
FIG. 34 shows a third stage of a method of using the metal detector of an access control system, in accordance with one embodiment of the present patent application.

Referring to FIGS. 33 and 34, in one embodiment, the visitor V approaches the walkthrough metal detector 200 and places his forehead in front of the skin temperature sensor 212 so that the walkthrough metal detector may obtain the skin temperature of the visitor V. If the recorded skin temperature is within the acceptable range, the visitor V is authorized to proceed through the walkthrough metal detector 200. If the recorded skin temperature is above the acceptable temperature range, the walkthrough metal detector will generate an audio and/or visual signal or alarm prompting the tending security personnel to either request the individual check their skin temperature again or deny the individual access to the controlled area.

Figure 35:
FIG. 35 shows a fourth stage of a method of using the metal detector of an access control system, in accordance with one embodiment of the present patent application.
Figure 36:
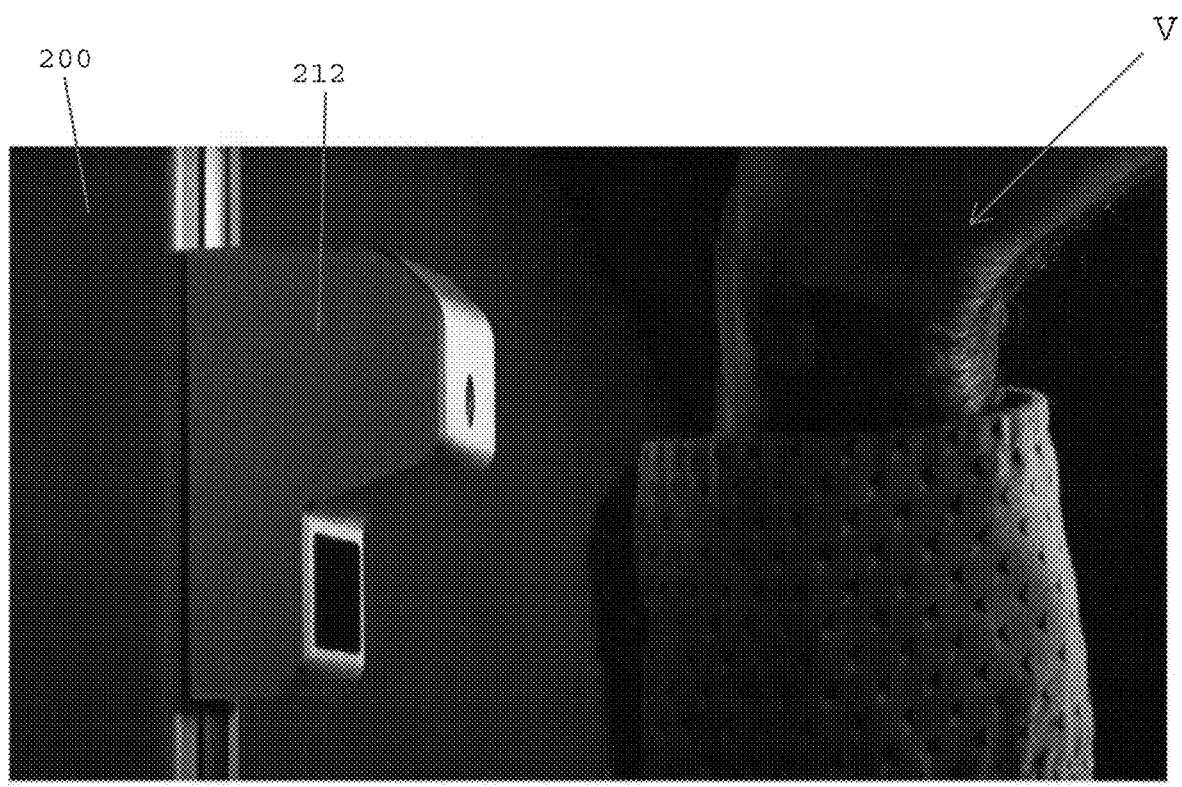
FIG. 36 shows a fifth stage of a method of using the metal detector of an access control system, in accordance with one embodiment of the present patent application.

Referring to FIGS. 35 and 36, in one embodiment, the visitor V approaches the walkthrough metal detector 200 and places their wrist in front of the skin temperature sensor 212 so that the walkthrough metal detector may obtain the skin temperature of the visitor V. If the recorded skin temperature is within the acceptable range, the visitor V is authorized to proceed through the walkthrough metal detector 200. If the recorded skin temperature is above the acceptable temperature range, the walkthrough metal detector will generate an alert signal or alarm and tending security will deny the visitor access to the controlled area beyond the walkthrough metal detector 200.

Figure 37:
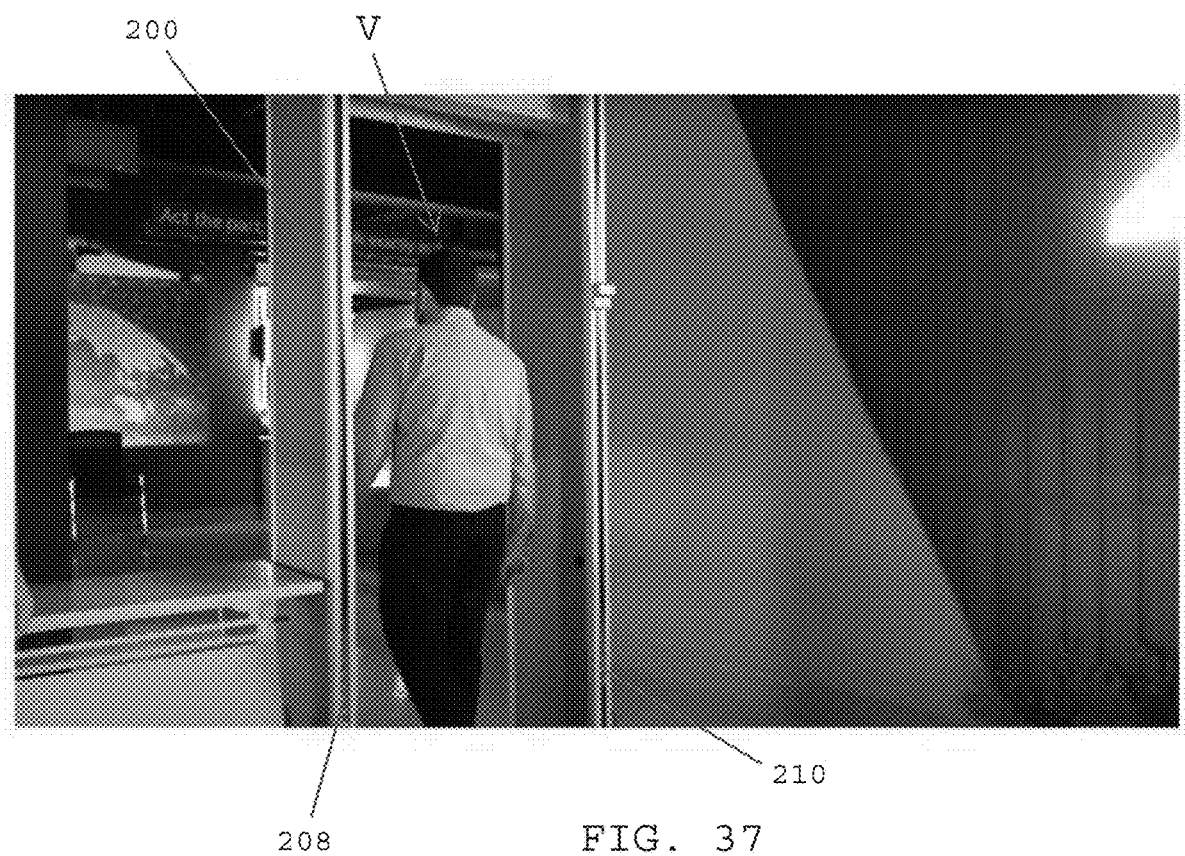
FIG. 37 shows a sixth stage of a method of using the metal detector of an access control system, in accordance with one embodiment of the present patent application.

Referring to FIG. 37, in one embodiment, after the visitor has been recorded as having an acceptable skin temperature, the visitor is authorized to proceed through the walkthrough metal detector 200. In FIG. 37, the walkthrough metal detector 200 detects that the visitor V is carrying a metal object. Upon detecting metal, the first and second LED light banks 208, 210 of the walkthrough metal detector 200 illuminate to notify tending security personnel that the visitor V is carrying a metal object.

Figure 38:
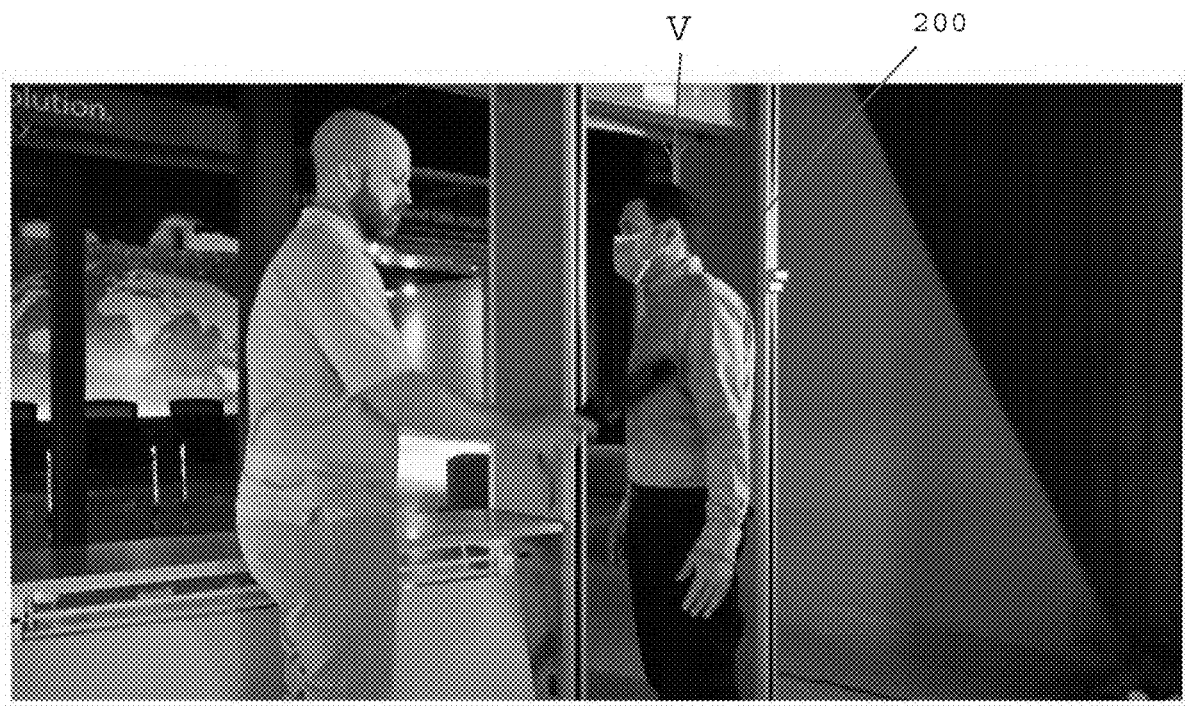
FIG. 38 shows a seventh stage of a method of using the metal detector of an access control system, in accordance with one embodiment of the present patent application.

Referring to FIG. 38, in one embodiment, because the walkthrough metal detector 200 alerted security personnel that the visitor V is carrying a metal object, the visitor V is required to return to the front side of the walkthrough metal detector 200 to undergo enhanced security screening including wanding with a handheld metal detector.

Figure 39:
FIG. 39 shows a first stage of a method of using a metal detector of an access control system, in accordance with one embodiment of the present patent application.
Figure 40:
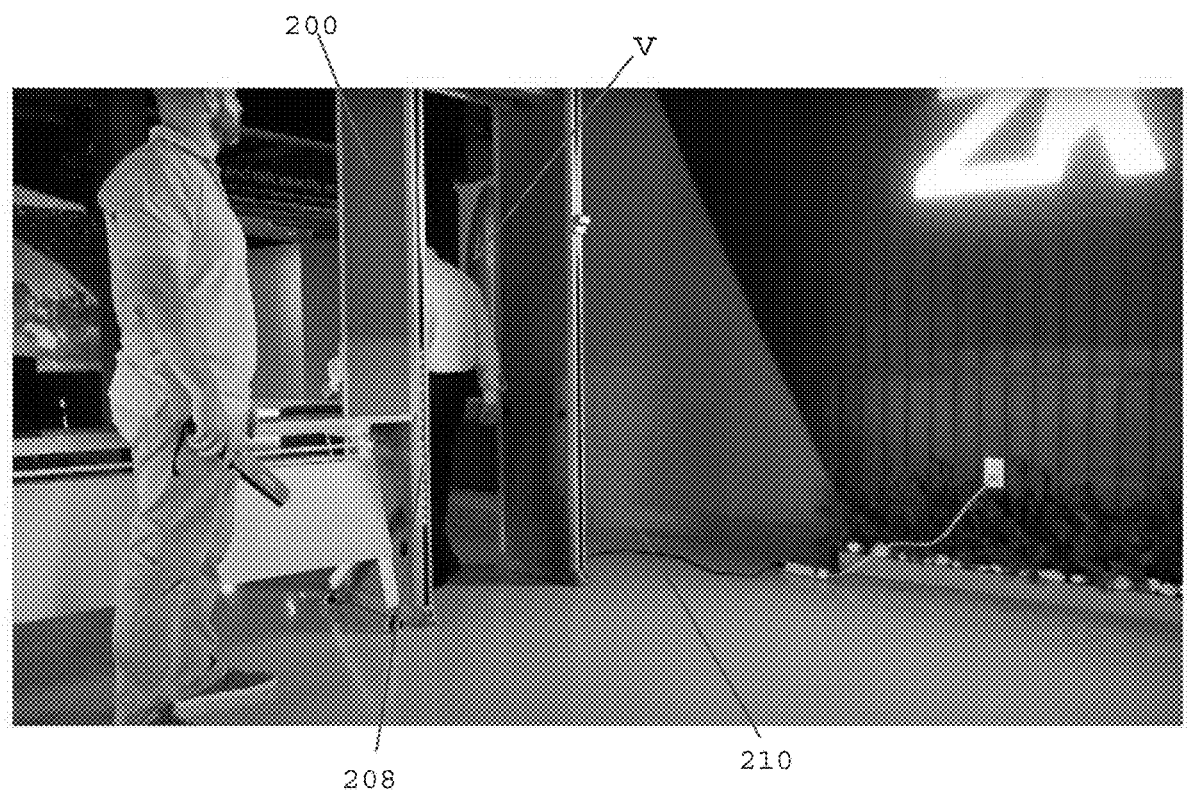
FIG. 40 shows a second stage of a method of using the metal detector of an access control system, in accordance with one embodiment of the present patent application.

Referring to FIGS. 39 and 40, in one embodiment, the first and second LED light banks 208, 210 of the walkthrough metal detector 200 are configured to illuminate in a manner that enables security personnel to quickly identify where the metal object is located on the visitor V (e.g., the left side of the body or the right side of the body). In FIG. 40, the first LED light bank 208 illuminates to alert tending security personnel that the visitor V is carrying a metal object of the left side of his body. The second LED light bank 210 is not illuminated because the visitor V is not carrying a metal object on the right side of his body.

Figure 41:
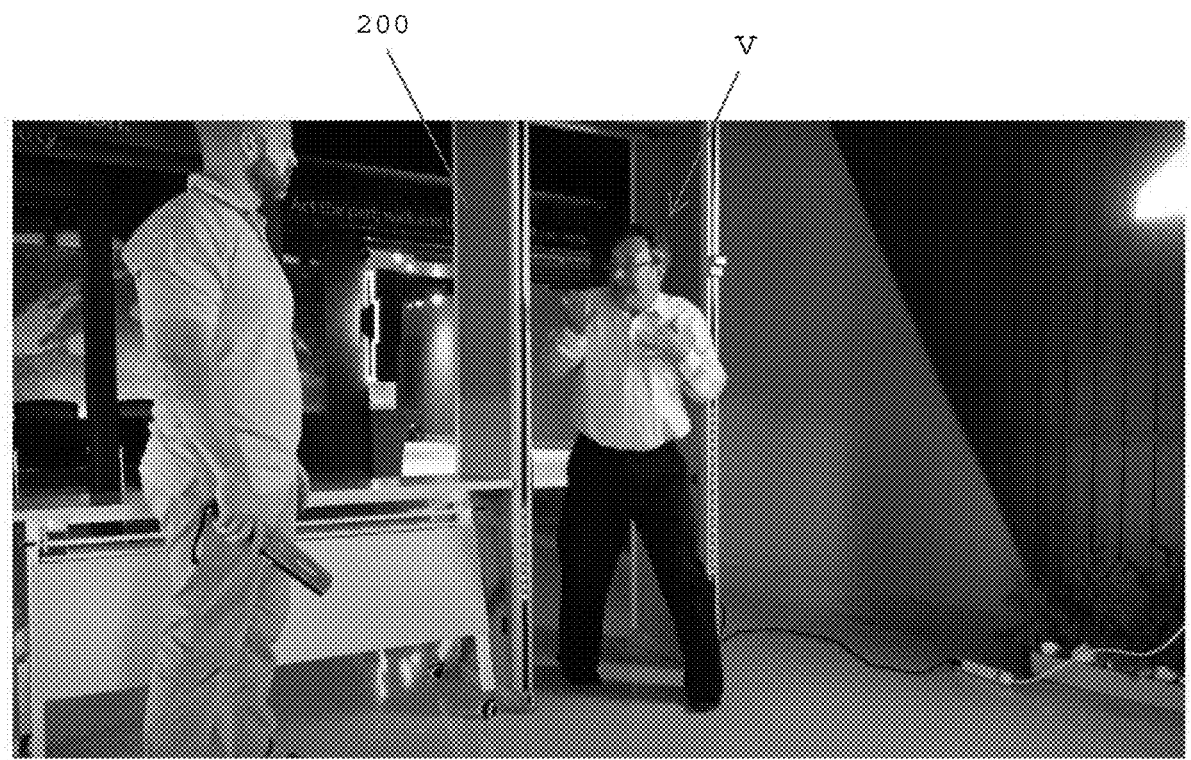
FIG. 41 shows a third stage of a method of using the metal detector of an access control system, in accordance with one embodiment of the present patent application.
Figure 42:
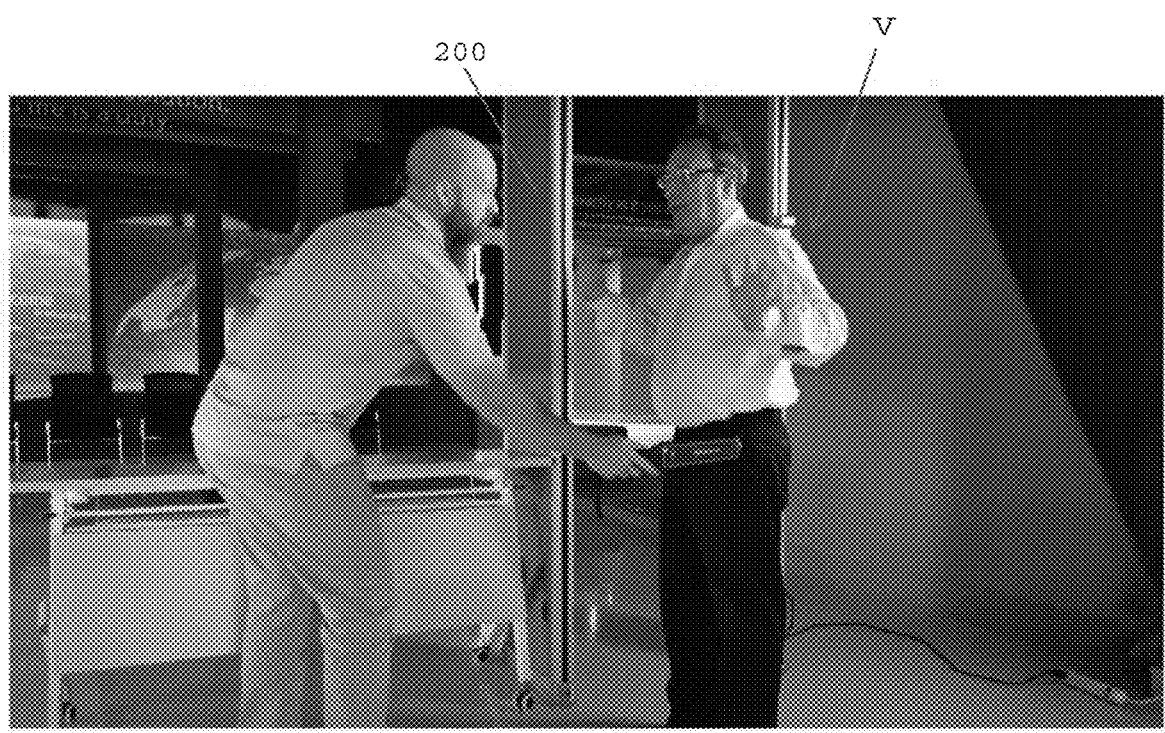
FIG. 42 shows a fourth stage of a method of using the metal detector of an access control system, in accordance with one embodiment of the present patent application.

Referring to FIGS. 41 and 42, after the walkthrough metal detector 200 has detected metal, the visitor V is required to return to the front side of the walkthrough metal detector for enhanced security screening, which includes wanding with a handheld metal detector. In FIG. 42, the tending security guard detects the metal object on the left side of the visitor, which is consistent with the illumination of the first LED light bank 208 (FIG. 40).

Figure 43:
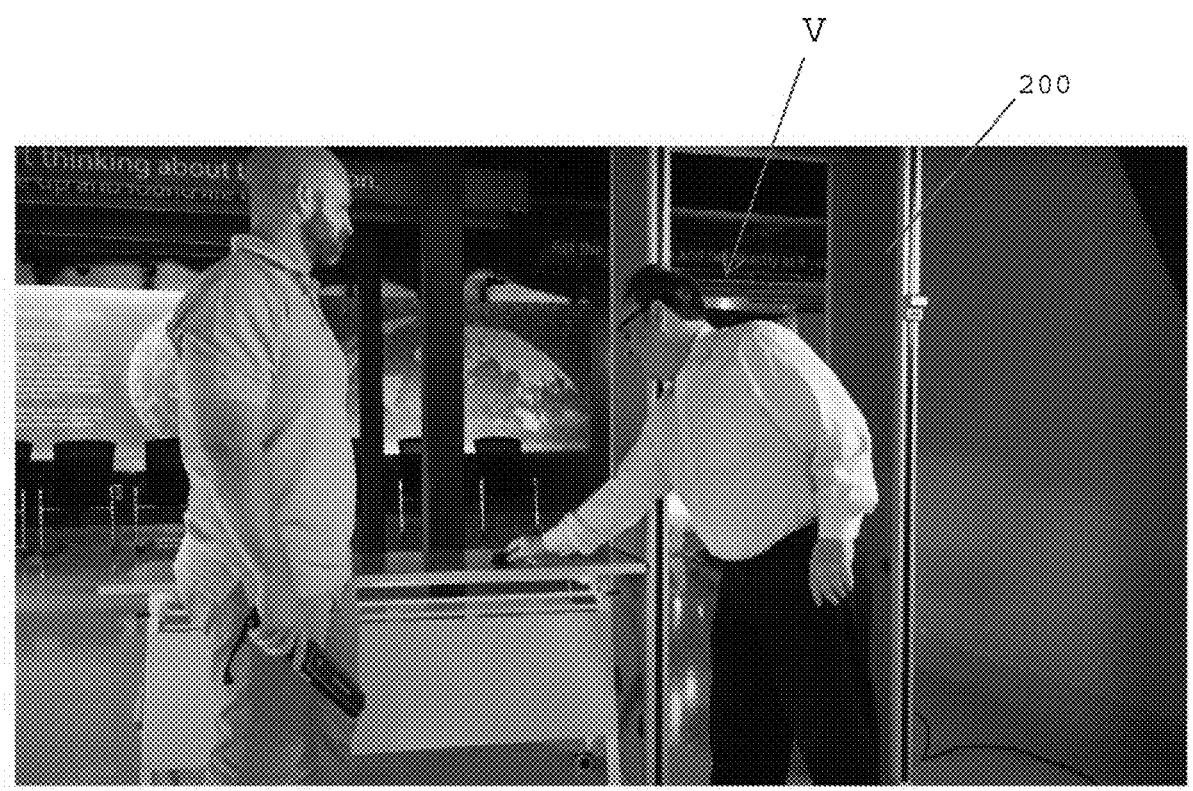
FIG. 43 shows a fifth stage of a method of using the metal detector of an access control system, in accordance with one embodiment of the present patent application.

Referring to FIG. 43, the visitor V removes the metal object (i.e., a cell phone) from his left front pocket and places the metal object on a security table. The visitor V is then authorized to pass through the walkthrough metal detector 200.

Figure 44:
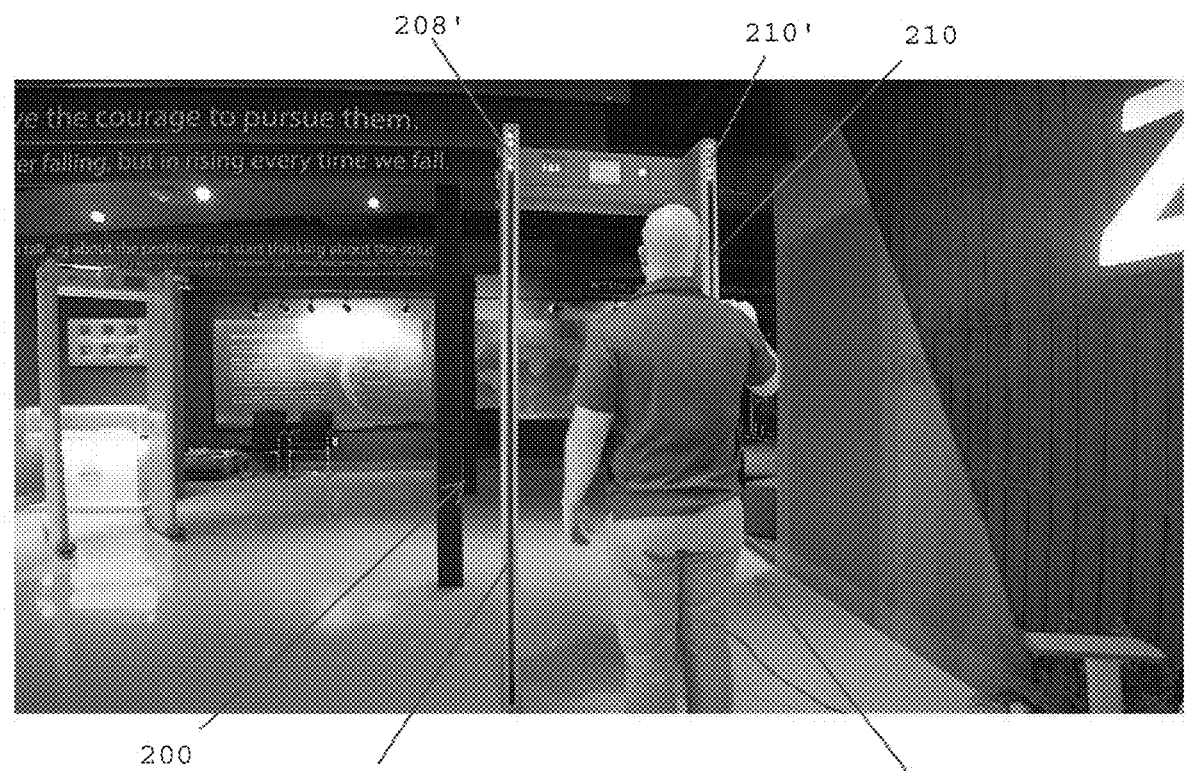
FIG. 44 shows a metal detector of an access control system, the metal detector having LEDs that are illuminated to provide an alert that an individual passing through the metal detector has been recorded as having an unacceptable skin temperature, in accordance with one embodiment of the present patent application.

Referring to FIG. 44, in one embodiment, a visitor V is attempting to pass through a walkthrough metal detector 200 and raises his wrist so that the skin temperature sensor 212 (FIG. 35) can obtain a skin temperature reading. The visitor V has an unacceptable temperature reading, which results in the illumination of the upper end sections 208' and 210' of the respective first and second LED light banks 208, 210 to provide an alert that the visitor has an unacceptable temperature. In one embodiment, when unacceptable temperature readings are obtained, only the upper end sections 208', 210' of the LED light banks are illuminated and the remaining sections of the LED light banks are not illuminated. This lighting pattern quickly notifies tending security personnel that a visitor has been recorded as having an unacceptable temperature.

Figure 45:
FIG. 45 shows a metal detector of an access control system, the metal detector having LEDs that are illuminated to provide an alert that an individual passing through the metal detector is carrying a metal object, in accordance with one embodiment of the present patent application.

Referring to FIG. 45, in one embodiment, a visitor V is attempting to pass through a walkthrough metal detector 200. The walkthrough metal detector 200 detects the presence of a metal object on the left side of the visitor V. In response, the walkthrough metal detector illuminates at least some of the LED lights of the first LED light bank 208 on the left side of the walkthrough metal detector to alert tending security personnel that the visitor V is carrying a metal object on his left side. The second LED light bank 210 on the right side of the walkthrough metal detector 200 is not illuminated because there are no metal objects on the right side of the visitor V. Providing an indication of whether the metal object is located on the left or right side of a visitor V enables security personnel to quickly locate where a metal object is located on a person, which allows the metal object to be quickly removed by security personnel for speeding up throughput at a walkthrough metal detector screening site.

Figure 46:
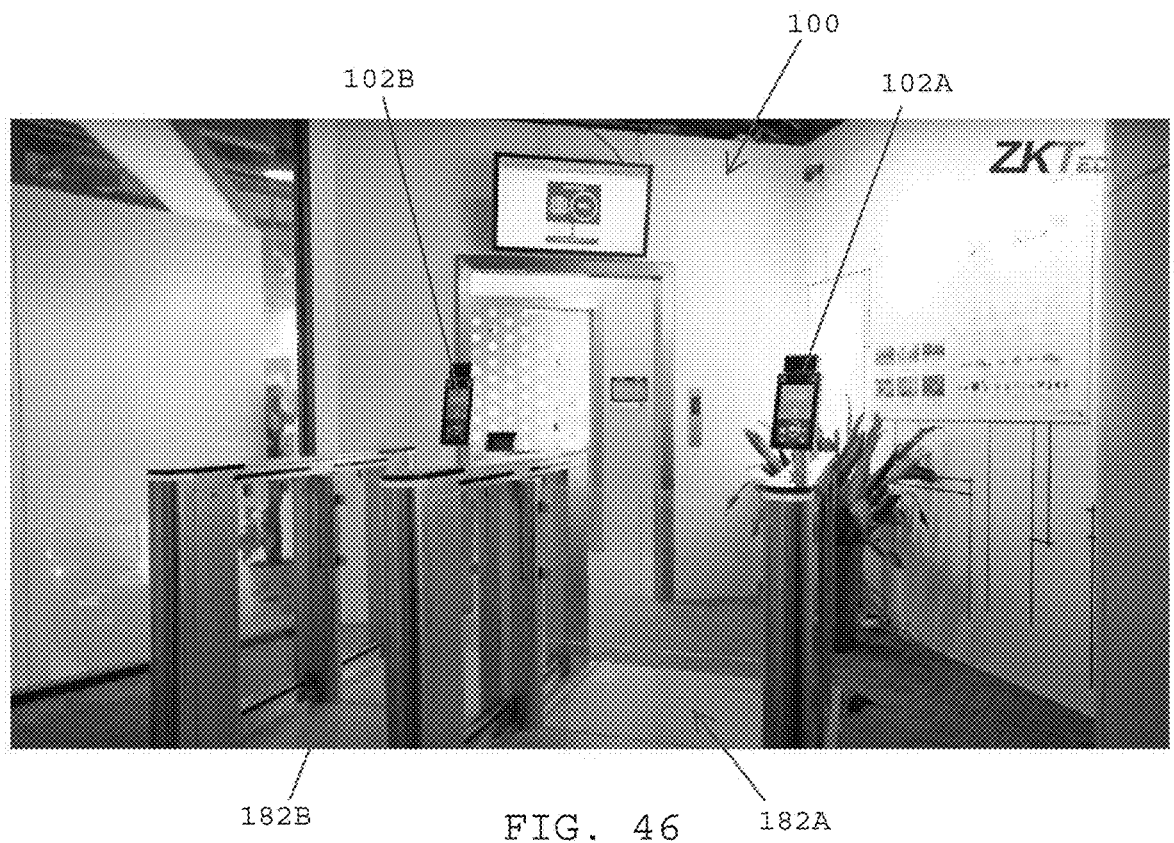
FIG. 46 is a perspective view of turnstiles and access control readers of an access control system that is used to count and control the maximum number of people that can occupy a physical space, in accordance with one embodiment of the present patent application.

Referring to FIG. 46, in one embodiment, an access control system 100 may be used for people counting and occupancy control within a controlled area. For example, the access control system may be used to control how many people may be inside a controlled area at any one time.

In one embodiment, the access control system 100 includes a turnstile 182 having a first access control reader 102A associated therewith for counting how many people enter a controlled area.

In one embodiment, the access control system includes the same turnstile 182 having a second access control reader 102B associated therewith for counting how many people exit the controlled area.

When an individual attempts to enter a controlled area, the access control system will open the gates of the turnstile 182 if the capacity limit of the controlled area has not been reached per the capacity limit rules established for the access control system. Once, the access control system determines that the capacity of the controlled area is less than the capacity limit, the access control system 100 will again enable the turnstile with the first access control reader 102A to open to allow individuals to enter the controlled area.

Figure 47:
FIG. 47 is a perspective view of one of an access control reader shown in FIG. 46.

Referring to FIG. 47, in one embodiment, the display screen 124 of the first access control reader 102A indicates that the capacity limit rules for the controlled area is 10 people, that six people are inside the controlled area, and that four more people may enter the controlled area until the capacity limit for the controlled area has been reached.

Figure 48:
FIG. 48 shows a first stage of a method of using an access control system to count and control the maximum number of people that can occupy a physical space, in accordance with one embodiment of the present patent application.

Referring to FIG. 48, the overhead display monitor 220 provides an indication that the capacity limit of the controlled area has not been reached and that more people may pass through the turnstile with access control reader 102A to enter the controlled area. In one embodiment, the overhead display monitor 220 has a section that is green to provide a color indicator that more people may enter the controlled area.

Figure 49:
FIG. 49 shows a second stage of a method of using an access control system to count and control the maximum number of people that can occupy a physical space, in accordance with one embodiment of the present patent application.

Referring to FIG. 49, the overhead display monitor 220 still provides an indication that the capacity limit of the controlled area has not been reached and that more people may pass through the turnstile with access control reader 102A to enter the controlled area. In one embodiment, the overhead display monitor 220 has a section that is yellow to provide a color indicator that the total number of people within the controlled area is getting close to the capacity limit.

Figure 50:
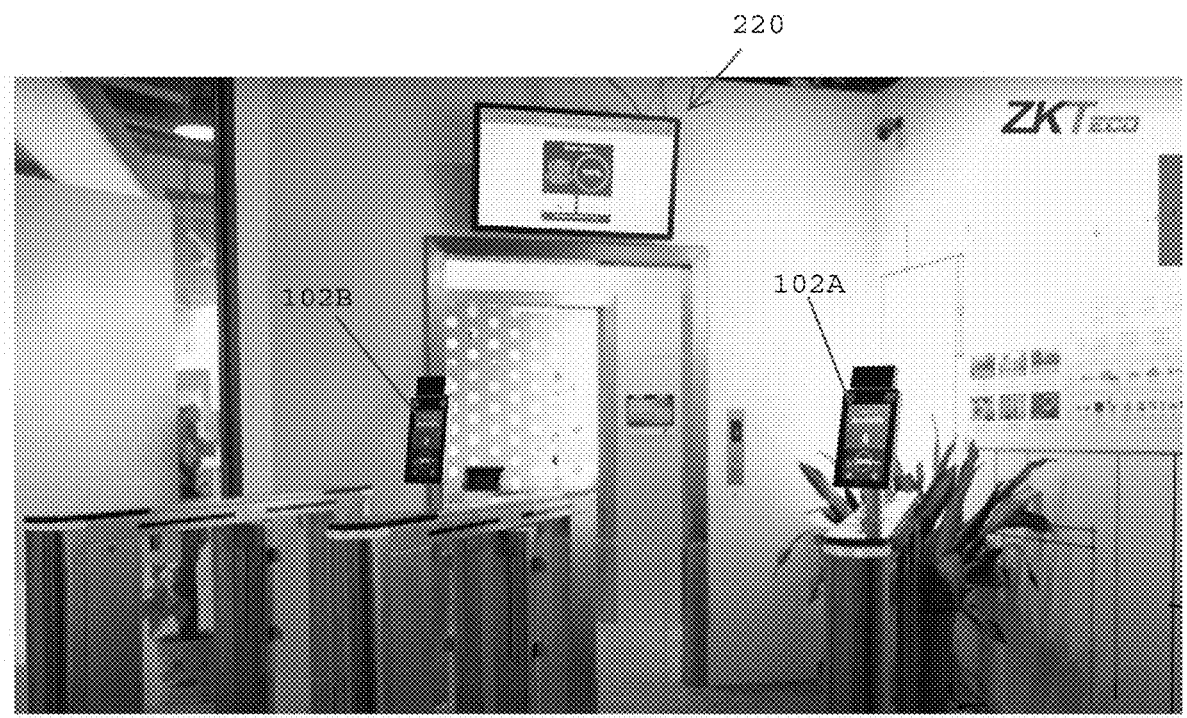
FIG. 50 shows a third stage of a method of using an access control system to count and control the maximum number of people that can occupy a physical space, in accordance with one embodiment of the present patent application.
Figure 51:
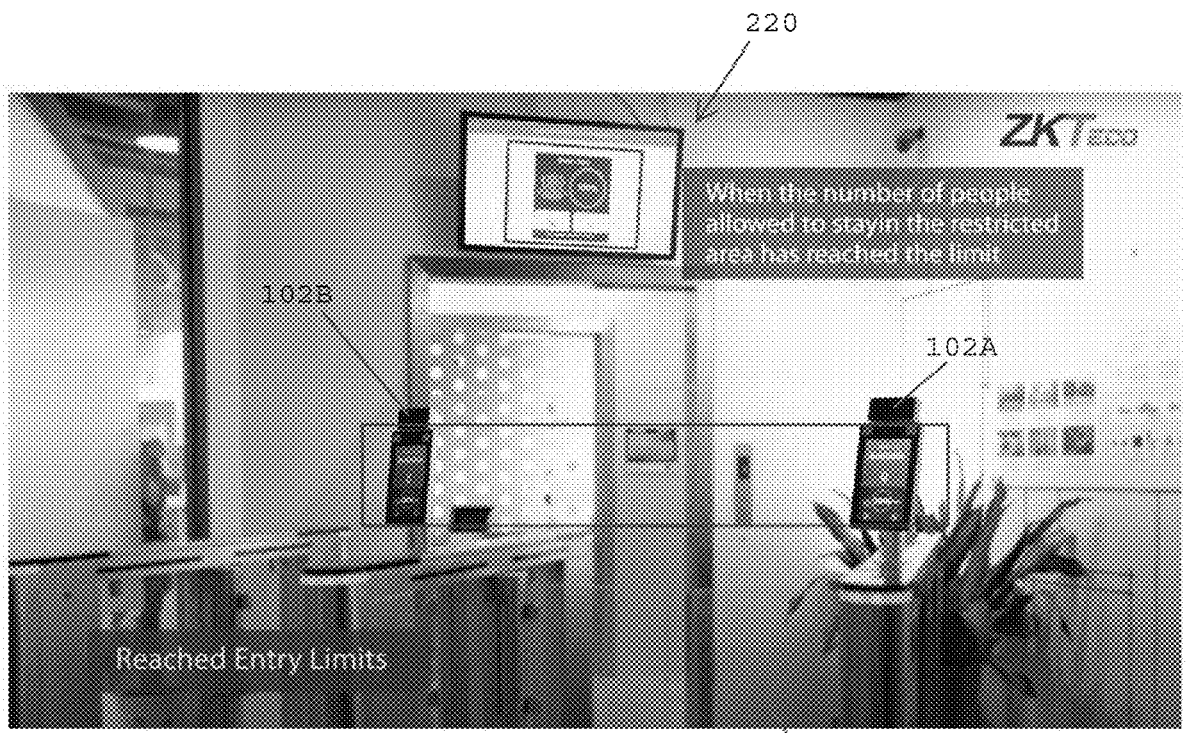
FIG. 51 shows a fourth stage of a method of using an access control system to count and control the maximum number of people that can occupy a physical space, in accordance with one embodiment of the present patent application.

Referring to FIGS. 50 and 51, when the number of people inside the controlled area matches the capacity limit for the controlled area, the overhead display monitor 220 and the first and second access control readers 102A, 102B display messages and a red color to indicate that the total number of people within the controlled area has matched the capacity limit. At this stage, the turnstile with access control reader 102A will not open to allow more people to enter the controlled area.

Figure 52:
FIG. 52 shows a fifth stage of a method of using an access control system to count and control the maximum number of people that can occupy a physical space, in accordance with one embodiment of the present patent application.

Referring to FIG. 52, with the controlled area at maximum capacity, a person attempts to enter the controlled area. The overhead display monitor 220 and the first and second access control readers 102A, 102B display messages and a red color to indicate that the total number of people within the controlled area has matched the capacity limit. At this stage, the turnstile with access control reader 102A will not open to allow more people to enter the controlled area. The person must wait until someone leaves the controlled area.

Figure 53:
FIG. 53 shows a sixth stage of a method of using an access control system to count and control the maximum number of people that can occupy a physical space, in accordance with one embodiment of the present patent application.
Figure 54:
FIG. 54 shows a seventh stage of a method of using an access control system to count and control the maximum number of people that can occupy a physical space, in accordance with one embodiment of the present patent application.
Figure 55:
FIG. 55 shows an eighth stage of a method of using an access control system to count and control the maximum number of people that can occupy a physical space, in accordance with one embodiment of the present patent application.

Referring to FIGS. 53-55, a person leaves the controlled area so that the controlled area is no longer at maximum capacity. The access control system then authorizes the person that is waiting to enter the controlled area. The gates of the turnstile will open to allow the person that is waiting to enter the controlled area.

Figure 56:
FIG. 56 shows a ninth stage of a method of using an access control system to count and control the maximum number of people that can occupy a physical space, in accordance with one embodiment of the present patent application.

Referring to FIG. 56, another person leaves the controlled area. The overhead display monitor and the access control readers 102A, 102B continue to indicate that the controlled area is not at maximum capacity and that additional people can enter the controlled area.

Figure 57:
FIG. 57 shows an audit record of an access control system used to count and control the maximum number of people that can occupy a physical space, in accordance with one embodiment of the present patent application.

Referring to FIG. 57, in one embodiment, the access control system preferably includes an audit record that provide identifying information about the people that are within a controlled area. In one embodiment, the identifying information may include but is not limited to identification numbers, first and last names, department assignment, card numbers, the time of entry into a controlled area, and the last access control reader that screened the individual.

Figure 58:
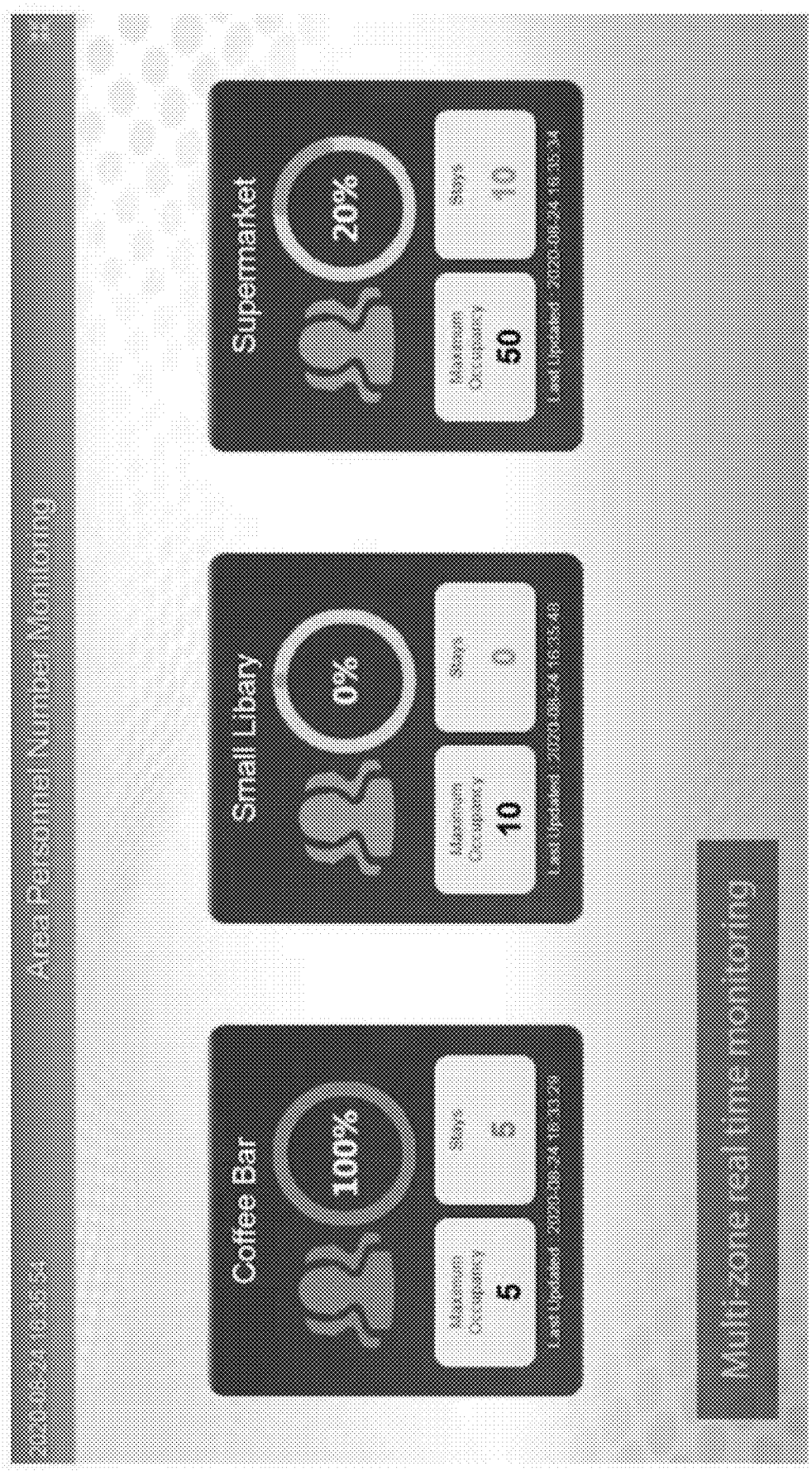
FIG. 58 shows a display screen of an access control system used to count and control the maximum number of people that can occupy physical spaces, in accordance with one embodiment of the present patent application.

Referring to FIG. 58, in one embodiment, the access control system may be used to assign different capacity limits for different controlled areas and to provide real-time feedback as to the number of people in each of the controlled areas.

In the embodiment of FIG. 58, a coffee bar has been assigned a maximum capacity limit of five people and the access control system indicates that five people are inside the coffee bar so that no additional people can enter the coffee bar until at least one person exits the coffee bar.

In the embodiment of FIG. 58, a small library has been assigned a maximum capacity limit of 10 people and the access control system indicates that there are zero people inside the small library so that up to 10 people can enter the small library.

In the embodiment of FIG. 58, a supermarket has been assigned a maximum capacity limit of 50 people and the access control system indicates that there are 10 people inside the supermarket so that up to 40 more people can enter the supermarket.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. An automated system for screening individuals comprising:
    an access control reader including one or more computer devices configured for screening a pre-registered individual seeking admittance into a controlled area;
    said one or more computer devices containing a facial recognition database that stores a facial record for said pre-registered individual;
    a camera system configured to capture a facial image of said pre-registered individual, wherein said one or more computer devices evaluate said captured facial image for determining whether said captured facial image matches said facial record of said pre-registered individual that is stored in said facial recognition database;
    a skin temperature sensor for obtaining a skin temperature reading for said pre-registered individual;
    wherein said one or more computer devices are configured to generate an electronic signal to admit said pre-registered individual into said controlled area if said captured facial image matches said facial record of said pre-registered individual that is stored in said facial recognition database and if said skin temperature reading for said pre-registered individual is within an acceptable skin temperature range established for said automated syste;
    said one or more computer devices containing software for a health-check screening questionnaire that is used for evaluating the health status of said pre-registered individual;
    wherein said pre-registered individual is authorized admittance into said controlled area if completion of said health-check screening questionnaire indicates that said pre-registered individual is healthy as defined by a predetermined standard;
    wherein said pre-registered individual is denied admittance into said controlled area if competition of said health-check screening questionnaire indicates that said pre-registered individual is unhealthy as defined by said predetermined standard.

2. The system as claimed in claim 1, further comprising an authenticating information generator that generates authenticating information that is used for confirming the identity of said pre-registered individual seeking admission to said controlled area.

3. The system as claimed in claim 2, further comprising;
said authenticating information generator comprising a OR code generator that is configured for transmitting a OR code to said pre-registered individual;
said access control reader comprising a OR code reader that is configured to scan said OR code that is transmitted to said pre-registered individual.

4. The system as claimed in claim 3, wherein said OR code generator is configured for transmitting said OR code to said pre-registered individual in an electronic format that is adapted for being displayed on an electronic device.

5. The system as claimed in claim 1, wherein said one or more computer devices operate software that is configured for analyzing said captured facial image for confirming whether said pre-registered individual is wearing a protective mask.

6. The system as claimed in claim 5, wherein said one or more computer devices authorize admission into said controlled area upon confirming that said pre-registered individual is wearing said protective mask and deny admission into said controlled area upon confirming that said pre-registered individual is not wearing said protective mask.

7. The system as claimed in claim 1, wherein said camera system comprises:
a first camera configured to capture a first facial image of said pre-registered individual within the visible light spectrum;
a second camera configured to capture a second facial image of said pre-registered individual within the infrared light spectrum, wherein said captured first and second facial images are processed by said one or more computer devices for determining that said captured first and second facial images match said facial record of said pre-registered individual that is stored in said facial recognition database.

8. The system as claimed in claim 1, further comprising:
a visitor management kiosk that contains said access control reader;
a printer configured to print an admittance ticket or badge for said pre-registered individual after said pre-registered individual has been authorized for admission into said controlled area;
a slot formed in a stand of said visitor management kiosk for dispensing said admittance ticket or badge.

9. The system as claimed in claim 1, further comprising:
said one or more computers comprising a software protocol for transmitting an alert message to a host for notifying said host that said pre-registered individual has been authorized admission into said controlled area.

10. The system as claimed in claim 1, further comprising:
said one or more computer devices containing a biometric database that stores a biometric record for said pre-registered individual;
a biometric scanner for capturing biometric formation about said pre-registered individual seeking admittance into said controlled area;
wherein said one or more computer devices generate a signal to admit said pre-registered individual into said controlled area if said captured biometric information matches said biometric record of said pre-registered individual that is stored in said biometric database.

11. The system as claimed in claim 10, wherein said biometric database includes biometric information selected from the group consisting of fingerprints, finger-vein patterns, facial patterns, palm vein patterns, palm prints, iris images, retina images, and voice recordings.

12. The system as claimed in claim 1, wherein said skin temperature sensor is selected from the group consisting of thermal sensors, sensors incorporating thermographic imaging technology, and sensors incorporating thermopile technology.

13. The system as claimed in claim 12, wherein said access control reader comprises:
a visual display including a first region for displaying said captured image of said pre-registered individual;
said visual display including a second region for displaying a thermal image of said pre-registered individual that has been captured by said skin temperature sensor.

14. The system as claimed in claim 1, further comprising a physical barrier that is in communication with said access control reader, wherein said physical barrier is moveable between a first position in which said pre-registered individual is prevented from proceeding toward said controlled area and a second position in which said pre-registered individual is free to pass through said physical barrier for proceeding toward said controlled area.

15. The system as claimed in claim 14, wherein said physical barrier is selected from the group of physical barriers consisting of turnstiles, gates, doors, and elevators.

16. An automated system for screening individuals comprising:
an access control reader including one or more computer devices configured for screening a pre-registered individual seeking admittance into a controlled area;
said one or more computer devices containing a facial recognition database that stores a facial record for said pre-registered individual;
a camera system configured to capture a facial image of said pre-registered individual, wherein said one or more computer devices evaluate said captured facial image for determining whether said captured facial image matches said facial record of said pre-registered individual that is stored in said facial recognition database,
a skin temperature sensor for obtaining a skin temperature reading for said pre-registered individual;
wherein said one or more computer devices are configured to generate an electronic signal to admit said pre-registered individual into said controlled area if said captured facial image matches said facial record of said pre-registered individual that is stored in said facial recognition database and if said skin temperature reading for said pre-registered individual is within an acceptable skin temperature range established for said automated system;
a metal detector including first and second vertical panels having upper ends that are joined together by a control module that extends between the upper ends of said two vertical panels;
said metal detector being adapted to detect metal passing between said first and second vertical panels;
said first vertical panel having a front side including a first LED light array that extends along the front side of said first vertical panel;
said second vertical panel having a front side including a second LED light array that extends along the front side of said second vertical panel;

wherein said skin temperature sensor is secured to said second vertical panel for obtaining said skin temperature reading for said pre-registered individual.

17. The system as claimed in claim 16, wherein said metal detector illuminates at least one LED light of said first and second LED light arrays if a metal object is detected between said first and second vertical panels.

18. The system as claimed in claim 17, wherein upon detecting a metal object passing between said first and second vertical panels, said metal detector illuminates an LED light that is nearest to said metal object.

* * * * *